(12) United States Patent
Anderson

(10) Patent No.: US 7,632,686 B2
(45) Date of Patent: Dec. 15, 2009

(54) HIGH SENSITIVITY QUANTITATION OF PEPTIDES BY MASS SPECTROMETRY

(75) Inventor: Norman L. Anderson, Washington, DC (US)

(73) Assignee: Anderson Forschung Group, Washington, DC (US)

( * ) Notice: Subject to any disclaimer, the term of this patent is extended or adjusted under 35 U.S.C. 154(b) by 0 days.

(21) Appl. No.: 10/676,005

(22) Filed: Oct. 2, 2003

(65) Prior Publication Data

US 2004/0072251 A1 Apr. 15, 2004

Related U.S. Application Data

(60) Provisional application No. 60/496,037, filed on Aug. 18, 2003, provisional application No. 60/449,190, filed on Feb. 20, 2003, provisional application No. 60/420,613, filed on Oct. 23, 2002, provisional application No. 60/415,499, filed on Oct. 3, 2002.

(51) Int. Cl.
| | |
|---|---|
| G01N 1/00 | (2006.01) |
| G01N 31/00 | (2006.01) |
| G01N 33/536 | (2006.01) |
| G01N 33/538 | (2006.01) |
| G01N 33/563 | (2006.01) |
| G01N 33/566 | (2006.01) |

(52) U.S. Cl. ............... 436/175; 435/4; 435/7.1; 435/39; 435/173.7; 435/174; 435/243; 436/8; 436/17; 436/86; 436/161; 436/174; 436/501; 436/513; 436/518; 436/536; 436/538; 436/540; 436/541

(58) Field of Classification Search ........... 435/7.1, 435/7.92, 7.95, 39, 174, 381; 436/57, 85, 436/86, 161, 164, 171, 172, 173, 174, 175, 436/501, 504

See application file for complete search history.

(56) References Cited

U.S. PATENT DOCUMENTS

| | | | |
|---|---|---|---|
| 5,955,729 A | 9/1999 | Nelson et al. | |
| 6,207,370 B1 * | 3/2001 | Little et al. ............ | 435/6 |
| 6,391,649 B1 | 5/2002 | Chait et al. | |
| 6,649,419 B1 | 11/2003 | Anderson | |
| 6,783,672 B2 | 8/2004 | Tubbs et al. | |
| 6,811,689 B2 | 11/2004 | Zhang et al. | |
| 6,864,099 B2 | 3/2005 | Regnier | |
| 6,872,575 B2 | 3/2005 | Regnier | |
| 6,974,704 B2 | 12/2005 | Nelson et al. | |
| 7,501,286 B2 | 3/2009 | Gygi et al. | |
| 2001/0312279 | 8/2001 | Gygi | |
| 2001/0021535 A1 | 9/2001 | Nelson et al. | |
| 2002/0037532 A1 | 3/2002 | Regnier et al. | |
| 2002/0055186 A1 | 5/2002 | Barry et al. | |
| 2002/0110904 A1 | 8/2002 | Nelson et al. | |
| 2002/0115056 A1 | 8/2002 | Goodlett | |
| 2002/0123055 A1 | 9/2002 | Estell et al. | |
| 2002/0127739 A1 | 9/2002 | Pieper et al. | |
| 2002/0164818 A1 | 11/2002 | Gruber et al. | |
| 2003/0044848 A1 | 3/2003 | Rush et al. | |
| 2003/0129769 A1 | 7/2003 | Regnier | |
| 2004/0029292 A1 | 2/2004 | Joos et al. | |
| 2004/0038307 A1 | 2/2004 | Lee et al. | |
| 2004/0043497 A1 | 3/2004 | Feuer et al. | |
| 2004/0072251 A1 | 4/2004 | Anderson | |
| 2004/0180380 A1 | 9/2004 | Lee et al. | |
| 2004/0214338 A1 | 10/2004 | Borchers | |
| 2004/0229283 A1 | 11/2004 | Gygi et al. | |
| 2005/0064422 A1 | 3/2005 | Barnidge et al. | |
| 2005/0069911 A1 | 3/2005 | Lee et al. | |
| 2005/0202506 A1 | 9/2005 | Cantor | |

FOREIGN PATENT DOCUMENTS

| | | |
|---|---|---|
| WO | WO 00/67017 | 11/2000 |
| WO | WO 01/86306 | 11/2001 |
| WO | WO03016861 | 2/2003 |
| WO | WO 03016861 | 2/2003 |
| WO | WO 03/102220 | 12/2003 |
| WO | WO 2004/013636 | 2/2004 |
| WO | WO 2006/128492 | 12/2006 |

OTHER PUBLICATIONS

Geng et al. 2000. J. of Chromatography. vol. 870:295-313.*
Niederkofler et al. 2001. Anal. Chem. vol. 73 : 3294-3299.*
Wall et al. 2000. Anal. Chem. vol. 72: 1099-1111.*
Zhang et al. 2001. Anal. Chem. vol. 73: 5142-5149.*

(Continued)

*Primary Examiner*—Mark Navarro
*Assistant Examiner*—JaNa Hines
(74) *Attorney, Agent, or Firm*—Perkins Cole LLP

(57) ABSTRACT

The instant invention provides an economical flow-through method for determining amount of target proteins in a sample. An antibody preparation (whether polyclonal or monoclonal, or any equivalent specific binding agent) is used to capture and thus enrich a specific monitor peptide (a specific peptide fragment of a protein to be quantitated in a proteolytic digest of a complex protein sample) and an internal standard peptide (the same chemical structure but including stable isotope labels). Upon elution into a suitable mass spectrometer, the natural (sample derived) and internal standard (isotope labeled) peptides are quantitated, and their measured abundance ratio used to calculate the abundance of the monitor peptide, and its parent protein, in the initial sample.

28 Claims, 6 Drawing Sheets

OTHER PUBLICATIONS

Geng et al. (J. of Chromatography A, 2000, vol. 870: p. 295-313).*
Riggs et al., (J. of Chromatography A, 2001, vol. 924: p. 359-368).*
Suckau et al., (PNAS, 1990, vol. 87:pp. 9848-9852).*
Geng et al. (J. of Chromatography B, 2001, vol. 752: p. 293-306).*
Zhao et al. (PNAS. 1996. vol. 93:4020-4024).*
Nelson et al., (1995. Ana. Chem).*
Lisek et al, Rapid Communications in Mass Spectrometry, vol. 3 (2): p. 43-46 (1989).
Geng et al, Journal of Chromatography A, vol. 870 p. 295-313 (2000).
Chang et al, Analytical Chemistry, vol. 76 p. 4472-4483 (2004).
Rush et al, Nature Biotechnology, vol. 23 (1) p. 94-101 (2005).
Neiderkofler et al, Analytical Chemistry, vol. 73 p. 3294-3299 (2001).
Labugger et al, Clinical Chemistry, vol. 49 (6) p. 873-879 (2003).
Scrivener et al, Proteomics, vol. 3. p. 122-128 (2003).
Peiper et al, Proteomics, vol. 3 p. 422-432 (2003).
Gerber et al, Proc. Natl. Acad. Sci. USA, vol. 100 (12) p. 6940-6945 (2003).
Warren et al, Analytical Chemistry, vol. 76 p. 4082-4092 (2004).
Raska et al, Journal of the American Society for Mass Spectrometry, vol. 14 p. 1076-1085 (2003).
Li et al, Molecular and Cellular Proteomics, vol. 1.2 p. 157-168 (2002).
Anderson et al, Journal of Proteome Research, vol. 3 p. 228-234 (2004).
Anderson et al, Journal of Proteome Research, vol. 3 p. 235-244 (2004).
Purification, KingFisher 96, New Product Brochure, pp. 28-33, 1996.
Dynabeads, Dynal Biotech, pp. 1-6, 2004.
Adkins, J. N. et al., "Toward a Human Blood Serum Proteome," Molecular & Cellular Proteomics 1.12, 2002, pp. 947-955, vol. 1.
Amini, A. et al., "Simplification of Complex Tryptic Digests for Capillary Electrophoresis by Affinity Selection of Histidine-Containing Peptides with Immobilised Metal Ion Affinity Chromatography," Journal of Chromatography B., 2002, pp. 35-44, vol. 772.
Anderson, N. L. et al., "The Human Plasma Proteome, History, Character, and Diagnostic Prospects," Molecular & Cellular Proteomics 1.11, 2002, pp. 845-867, vol. 1.
Anderson, N. L. et al., "The Human Plasma Proteome, A Nonredundant List Developed by Combination of Four Separate Sources," Molecular & Cellular Proteomics 3.4, 2004, pp. 311-326, vol. 3.
Anderson, N. G. et al., "Analytical Techniques for Cell Fractions, XIX, The Cyclum: An Automatic System for Cyclic Chromatography," Analytical Biochemistry, 1975, pp. 159-174, vol. 66.
Anderson, N. G. et al., "Analytical Techniques for Cell Fractions, XX, Cyclic Affinity Chromatography: Principles and Applications," Analytical Biochemistry, 1975, pp. 371-393, vol. 68.
Anderson, L. et al., "High Resolution Two-Dimensional Electrophoresis of Human Plasma Proteins," Proc. Natl. Acad. Sci. USA, Dec. 1977, pp. 5421-5425, vol. 74, No. 12.
Anderson, N. L. et al., "Global Approaches to Quantitative Analysis of Gene-Expression Patterns Observed by use of Two-Dimensional Gel Electrophoresis," Clinical Chemistry, 1984, pp. 2031-2036, vol. 30, No. 12.
Anderson, N. L. et al., "Effects of Toxic Agents at the Protein Level: Quantitative Measurement of 213 Mouse Liver Proteins Following Xenobiotic Treatment," Fundamental and Applied Toxicology, 1987, pp. 39-50, vol. 8.
Anderson, N. L. et al., "A Two-Dimensional Gel Database of Human Plasma Proteins," Electropharesis, 1991, pp. 883-906, vol. 12.
Anderson, L. et al., "Effects of Oltipraz and Related Chemoprevention Compounds on Gene Expression in Rat Liver," 1995, J. Cell Biochem, pp. 108-116, Supplement 22.
Anderson, N. L., et al., "The Effects of Peroxisome Proliferators on Protein Abundances in Mouse Liver," Toxicology and Applied Pharmacology, 1996, pp. 75-89, vol. 137.
Beynon, R. J. et al., "Multiplexed Absolute Quantification in Proteomics using Artificial QCAT Proteins of Concafenated Signature Peptides," Nature Methods, Aug. 2005, pp. 587-589, vol. 2, No. 8.

Biswal, S. L. et al., "Micromixing with Linked Chains of Paramagnetic Particles," Analytical Chemistry, Nov. 1, 2004, pp. 6448-6455, vol. 76, No. 21.
Burroughs, N. J. et al., "Discriminating Self From Nonself with Short Peptides from Large Proteomes," Immunogenetics, 2004, pp. 311-320, vol. 56.
Chakraborty, A. et al., "Global Internal Standard Technology for Comparative Proteomics," Journal of Chromatography A, 2002, pp. 173-184, vol. 949.
Doherty, N. S. et al., "Analysis of Changes in Acute-Phase Plasma Proteins in an Acute Inflammatory Response and in Rheumatoid Arthritis Using Two-Dimensional Gel Electrophoresis," Electrophoresis, 1998, pp. 355-363, vol. 19.
Geng, M. et al., "Proteomics of Glycoproteins Based on Affinity Selection of Glycopeptides from Tryptic Digests," Journal of Chromatography B, 2001, pp. 293-306, vol. 752.
Hurst, G. B. et al., "Analysis for TNF-α Using Solid-Phase Affinity Capture with Radiolabel and MALDI-MS Detection," Analytical Chemistry, Oct. 15, 1999, pp. 4727-4733, vol. 71, No. 20.
Ji, J. et al., "Strategy for Qualitative and Quantitative Analysis in Proteomics Based on Signature Peptides," Journal of Chromatography B, 2000, pp. 197-210, vol. 745.
Kiselar, J. G. et al., "Direct Identification of Protein Epitopes by Mass Spectrometry Without Immobilization of Antibody and Isolation of Antibody—Peptide Complexes," Analytical Chemistry, May 1, 1999, pp. 1792-1801, vol. 71, No. 9.
Lacey, J. M. et al., "Rapid Determination of Transferrin Isoforms by Immunoaffinity Liquid Chromatography and Electrospray Mass Spectrometry," Clinical Chemistry, 2001, pp. 513-518, vol. 47, No. 3.
Lipton, M. S. et al., "Global Analysis of the *Deinococcus radiodurans* Proteome by Using Accurate Mass Tags," PNAS, Aug. 20, 2002, pp. 11049-11054, vol. 99, No. 17.
Maccoss, M. J. et al., "Shotgun Identification of Protein Modifications from Protein Complexes and Lens Tissue," PNAS, Jun. 11, 2002, pp. 7900-7905, vol. 99, No. 2.
Munchbach, M. et al., "Quantitation and Facilitated de Novo Sequencing of Proteins by Isotopic N-Terminal Labeling of Peptides with a Fragmentation-Directing Moiety," Analytical Chemistry, Sep. 1, 2000, pp. 4047-4057, vol. 72, No. 17.
Nedelkov, D. et al., "Design of Buffer Exchange Surfaces and Sensor Chips for Biosensor Chip Mass Spectrometry," Proteomics, 2002. pp. 441-446, vol. 2.
Nelson, R. W. et al., "BIA/MS of Epitope-Tagged Peptides Directly from *E. coli* Lysate: Multiplex Detection and Protein Identification at Low-Femtomole to Subfemtomole Levels," Analytical Chemistry, 1999, pp. 2858-2865, vol. 71.
Oda, Y. et al., "Accurate Quantitation of Protein Expression and Site-Specific Phosphorylation," Proc. Natl. Acad. Sci. USA, Jun. 1999, pp. 6591-6596, vol. 96.
Ong, S. E. et al., "Stable Isotope Labeling by Amino Acids in Cell Culture, SILAC, as a Simple and Accurate Approach to Expression Proteomics," Molecular & Cellular Proteomics 1.5, 2002, pp. 376-386, vol. 1.
Petricoin, E. F. III. et al., Use of Proteomic Patterns in Serum to Identify Ovarian Cancer, The Lancet, Feb. 16, 2002, pp. 572-577, vol. 359.
Qiu, Y. et al., "Acid-Labile Isotope-Coded Extractants: A Class of Reagents for Quantitative Mass Spectrometric Analysis of Complex Protein Mixtures," Analytical Chemistry, Oct. 1, 2002, pp. 4969-4979, vol. 74, No. 19.
Rida, A. et al., "Manipulation of Self-Assembled Structures of Magnetic Beads for Microfluidic Mixing and Assaying," Analytical Chemistry, Nov. 1, 2004, pp. 6239-6246, vol. 76, No. 21.
Riggs, L. et al., "Automated Signature Peptide Approach for Proteomics," Journal of Chromatography A, 2001, pp. 359-368, vol. 924.
Robertson, E. A. et al., "Biochemical Individuality and the Recognition of Personal Profiles with a Computer," Clinical Chemistry, 1980, pp. 30-36, vol. 26, No. 1.
Rudiger, A.-H. et al., "Affinity Mass Spectrometry-Based Approaches for the Analysis of Protein-Protein Interaction and Complex Mixtures of Peptide-Ligands," Analytical Biochemistry, 1999, pp. 162-170, vol. 275.

Safarik, I. et al, "Magnetic Techniques for the Isolation and Purification of Proteins and Peptides," BioMagnetic Research and Technology, 2004, pp. 1-17, vol. 2, No. 7.

Shevchenko, A. et al., "Deciphering Protein Complexes and Protein Interaction Networks by Tandem Affinity Purification and Mass Spectrometry," Molecular & Cellular Proteomics 1.3, 2002, pp. 204-212, vol. 1.

Suckau, D. et al., "Molecular Epitope Identification by Limited Proteolysis of an Immobilized Antigen-Antibody Complex and Mass Spectrometric Peptide Mapping," Proc. Natl. Acad. Sci. USA, Dec. 1990, pp. 9848-9852, vol. 87.

Suzuki, H. et al., "A Chaotic Mixer for Magnetic Bead-Based Micro Cell Sorter," Journal of Microelectromechanical Systems, Oct. 2004, pp. 779-790. vol. 13. No. 5.

Villaneuva, J. et al., "Serum Peptide Profiting by Magnetic Particle-Assisted, Automated Sample Processing and MALDI-TOF Mass Spectrometry," Analytical Chemistry, Mar. 15, 2004, pp. 1560-1570, vol. 76, No. 6.

Wang, S. et al., "Proteomics Based on Selecting and Quantifying Cysteine Containing Peptides by Covalent Chromatography," Journal of Chromatography A., 2001, pp. 345-357, vol. 924.

Wang, S. et al., "Quantitative Proteomics Strategy Involving the Selection of Peptides Containing both Cysteine and Histidine from Tryptic Digests of Cell Lysates," Journal of Chromatography A, 2002, pp. 153-162, vol. 949.

Wu, S-L. et al., "Targeted Proteomics of Low-Level Proteins in Human Plasma by LC/MS: Using Human Growth Hormone as a Model System," Journal of Proteome Research, 2002, pp. 459-465, vol. 1.

Yao, X. et al., "Proteolytic $^{18}$O Labeling for Comparative Proteomics: Model Studies with Two Serotypes of Adenovirus," Analytical Chemistry, Jul. 1, 2001, pp. 2836-2842, vol. 73, No. 13.

Yu, L. et al., "Epitope Mapping of Monoclonal Antibodies by Mass Spectrometry: Identification of Protein Antigens in Complex Biological Systems," J. Am. Soc. Mass. Spectrom., 1998, pp. 208-215, vol. 9.

Zhao, Y. et al., "Mapping Protein-Protein Interactions by Affinity-Directed Mass Spectrometry," Proc. Natl. Acad. Sci. USA, Apr. 1996, pp. 4020-4024, vol. 93.

U.S. Appl. No. 60/334,325, filed Nov. 29, 2001, Lindall et al.

Barr, J. R. et al., "Isotope Dilution-Mass Spectrometric Quantification of Specific Proteins: Model Application with Apolipoprotein A-I," Clinical Chemistry, 1996, pp. 1676-1682, vol. 42(10).

Bergen, H. R. et al., "Online Single-Step Analysis of Blood Proteins: The Transferrin Story," Analytical Biochemistry, 2001, pp. 122-129, vol. 296.

Clarke, N. J. et al., "Detection and Quantitation of Cellularly Derived Amyloid β Peptides by Immunoprecipitation-HPLC-MS," FEBS Letters, 1998, pp. 419-423, vol. 430.

Griffin, T. J. et al., "Toward a High-Throughput Approach to Quantitative Proteomic Analysis: Expression-Dependent Protein Identification by Mass Spectrometry," J. Am. Soc. Mass Spectrom., 2001, pp. 1238-1246, vol. 12.

Gygi, S. P. et al., "Proteome Analysis of Low-Abundance Proteins Using Multidimensional Chromatography and Isotope-Coded Affinity Tags," Journal of Proteome Research, 2002, pp. 47-54, vol. I.

Gygi, S. P. et al., "Quantitative Analysis of Complex Protein Mixtures using Isotope-Coded Affinity Tags," Nature Biotechnology, Oct. 1999, pp. 994-999, vol. 17.

Gygi, S. P. et al., "Mass Spectrometry and Proteomics," Current Opinion in Chemical Biology, 2000, pp. 489-494, vol. 4.

Kalkum, M. et al., "Detection of Secreted Peptides by Using Hypothesis-Driven Multistage Mass Spectrometry," PNAS, Mar. 4, 2003, pp. 2795-2800, vol. 100, No. 5.

Kiernan, U. A. et al., "High-Throughput Analysis of Human Plasma Proteins," American Biotechnology Laboratory, Mar. 2002, pp. 26, 28.

Kiernan, U. A. et al., "High-Throughput Protein Characterization Using Mass Spectrometric Immunoassay," Analytical Biochemistry, 2002, pp. 49-56, vol. 301.

Kiernan, U. A. et al., "Comparative Phenotypic Analyses of Human Plasma and Urinary Retinol Binding Protein Using Mass Spectrometric Immunoassay," Biochemical and Biophysical Research Communications, 2002, pp. 401-405, vol. 297.

Kippen, A. D. et al., "Development of an Isotope Dilution Assay for Precise Determination of Insulin, C-peptide, and Proinsulin Levels in Non-Diabetic and Type II Diabetic Individuals with Comparison to Immunoassay," The Journal of Biological Chemistry, May 9, 1997, pp. 12513-12522, vol. 272, No. 19.

Kiselar, J. G. et al., "Antigenic Surveillance of the Influenza Virus by Mass Spectrometry," Biochemistry, 1999, pp. 14185-14191, vol. 38.

Kiselar, J. G. et al., "Preservation and Detection of Specific Antibody-Peptide Complexes by Matrix-Assisted Laser Desorption Ionization Mass Spectrometry," J. Am. Soc. Mass Spectrom., 2000, pp. 746-750, vol. 11.

Miller, E. J. et al., "Quantitation of Type I, Ill, and V Collagens in Human Tissue Samples by High-Performance Liquid Chromatography of Selected Cyanogen Bromide Peptides," Analytical Biochemistry, 1991, pp. 54-60, vol. 196.

Regnier, F. E. et al., "Comparative Proteomics Based on Stable Isotope Labeling and Affinity Selection," Journal of Mass Spectrometry, 2002, pp. 133-145, vol. 37.

Stemmann, O. et al., "Dual Inhibition of Sister Chromatid Separation at Metaphase," Cell, Dec. 14, 2001, pp. 715-726, vol. 107.

Stewart, I. I. et al., "$^{18}$O Labeling: A Tool for Proteomics," Rapid Communications in Mass Spectrometry, 2001, pp. 2456-2465, vol. 15.

Tubbs, K. A. et al., "Detection and Quantification of β-2-Microglobulin Using Mass Spectrometric Immunoassay," Analytical Biochemistry, 2001, pp. 26-35, vol. 289.

Van Den Akker, C. R. et al., "Recycling Immobilized Antibodies," Clinical Chemistry, 1981, pp. 1954-1955, vol. 27, No. 11.

Supplementary European Search Report dated Jan. 9, 2007, 4 pages.

"Quantitative Assay of Methionine Enkephalin and β -Endorphin in Pituitary," Foreign Medical Sciences Section on Pharmacy, Jun. 1999, pp. 173-176, vol. 26(3).

"New Frontline in Research of Proteome: Quantitative Proteomics," ACTA Biochimica et Biophysica Sinica, 2001, pp. 477, 479, vol. 33(5).

Tanaka, T. et al., "Secretory Production of Recombinant Human C-Reactive Protein in Escherichia coli, capable of binding with phosphorylcholine, and its characterization," Biochemical and Biophysical Research Communications, 2002, pp. 163-166, vol. 295.

Gronborg, M. et al., "A Mass Spectrometry-Based Proteomic Approach for Identification of Serine/Threonine-Phosphorylated Proteins by Enrichment with Phospho-Specific Antibodies," Molecular & Cellular Proteomics, 2002, pp. 517-527, vol. I.

Ibarrola, N. et al., "A Proteomic Approach for Quantitation of Phosphorylation Using Stable Isotope Labeling in Cell Culture," Analytical Chemistry, Nov. 15, 2003, pp. 6043-6049, vol. 75, No. 22.

Everley, P. A. et al., "Quantitative Cancer Proteomics: Stable Isotope Labeling with Amino Acids in Cell Culture (SILAC) as a Tool for Prostate Cancer Research," Molecular & Cellular Proteomics, Jul. 2004, pp. 729-735, vol. 3.

Mayo, K. H., "Recent Advances in the Design and Construction of Synthetic Peptides: For the Love of Basics or Just for the Technology of It," TIBTECH, May 2000, pp. 212-217, vol. 18.

Lamla, T. et al., "The Cell-Free Protein Biosynthesis—Applications and Analysis of the System," Acta Biochimica Polonica, 2001, pp. 453-465, vol. 48, No. 2.

Anderson, L., "Candidate-Based Proteomics in the Search for Biomarkers of Cardiovascular Disease," J. Physiol, 2005, pp. 23-60, vol. 563.1.

International Search Report for International Application No. PCT/US05/19932, mailed Oct. 10, 2006, 5 pages.

Kuhn, E. et al., "Quantification of C-Reactive Protein in the Serum of Patients with Rheumatoid Arthritis Using Multiple Reaction Monitoring Mass Spectrometry and $^{13}$C-Labeled Peptide Standards," Proteomics, 2004, pp. 1175-1186, vol. 4.

"Cyanogen Bromide and Formic Acid Peptide Mapping." Protocol from: Skopp, R. N. et al., "Fingerprinting of Proteins Cleaved in Solution by Cyanogen Bromide," Appl. and Theoret. Electrophoresis, 1989, pp. 61-64, vol. 1.

"Cardiovascular," Merriam-Webster Dictionary, 2007.

Human CRP Sequence in NCBI AAL-48218, 2001.

Ong, S. et al., "Properties of $^{13}$C-Substituted Arginine in Stable Isotope Labeling by Amino Acids in Cell Structure (SILAC)," Journal of Proteome Research, 2003, pp. 173-181, vol. 2.

U.S. Appl. No. 60/312,279, Gygi, Seven P. et al.

Nelson et al., BIA/MS of Epitope-Tagged Peptides Directly from *E. coli* Lysate: . . . Analytical Chemistry 71:2858-2865 (1999).

Email from Randall Nelson to Paul M. Booth dated Wed. Jan. 14, 2009 at 18:20; Subject of email: U.S. Appl. No. 10/676,005.

Wall et al., Analytical Chemistry 72:1099-1111 (2000).

* cited by examiner

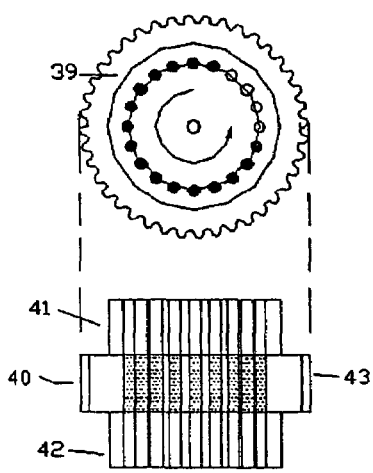
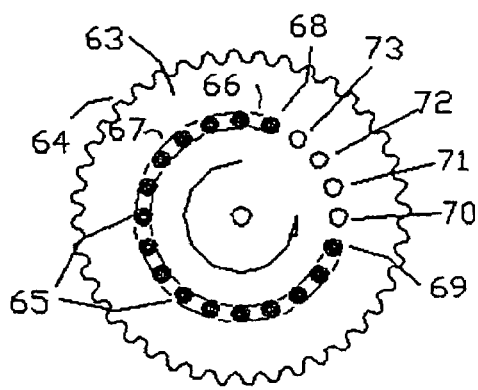
Figure 5.            Figure 6.
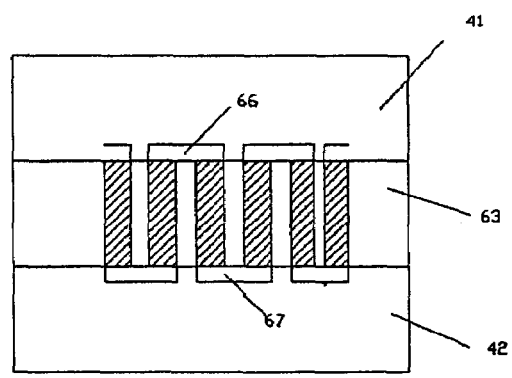
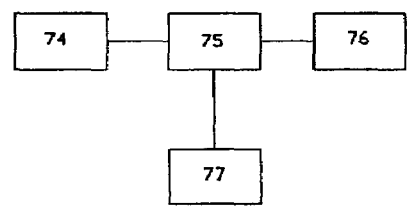
Figure 6b.           Figure 7.

HIGH SENSITIVITY QUANTITATION OF PEPTIDES BY MASS SPECTROMETRY

This application claims priority from U.S. Provisional Patent Application No. 60/496,037 filed on Aug. 18, 2003; U.S. Provisional Patent Application No. 60/449,190 filed on Feb. 20, 2003; U.S. Provisional Patent Application No. 60/420,613 filed on Oct. 23, 2002; and U.S. Provisional Patent Application No. 60/415,499 filed on Oct. 3, 2002.

FIELD AND BACKGROUND OF THE INVENTION

This invention relates to quantitative assays for evaluation of proteins in complex samples such as human plasma. The invention can be used both for analysis of samples from a single individual source or, for purposes of evaluating the level of a particular protein in a population, can be used to analyze pooled samples from the target population.

There is a need for quantitative assays for proteins in various complex protein samples, e.g., in human plasma. Conventionally these assays have been implemented as immunoassays, making use of specific antibodies against target proteins as specificity and detection reagents. New methods, particularly involving internal standardization with isotopically labeled peptides, allow mass spectrometry (MS) to provide such quantitative peptide and protein assays (as MS does in the measurement of low molecular weight drug metabolites currently). However there remains an issue of the dynamic range and sensitivity of MS assays when applied to very complex mixtures, such as those created by digestion of whole plasma protein to peptides. The present invention addresses this problem by providing improvements in sensitivity and by effectively equalizing the abundances of monitor peptides in a digest of a sample containing high and low abundance proteins thereby allowing measurement of both low and high abundance proteins in a complex sample.

One important advance that can help expand the diagnostically useful proteome is the use of many protein measurements together as a panel, so that patterns of change can be associated with disease or treatment, instead of relying on single protein markers interpreted alone. Several streams of scientific effort have generated data supporting this approach. (See Jellum, Bjornson, Nesbakken, Johansson, and Wold, *J Chromatogr* 217:231-7, 1981.) There were efforts to use the latter approach to detect disease signatures in then-standard 20-analyte serum chemistry panels, but these met with little success, probably due to the indirect character and small number of the analytes.

The concept and utility of multivariate protein markers has been established for some time. What requires comment is why this approach has not penetrated significantly into clinical practice.

While proteomics can demonstrate and sometimes measure many proteins, the prior art techniques (e.g., 2D gels) have been difficult to apply to a number of samples large enough to prove a clinical correlation at the research level. The alternative approach using existing tests is generally too expensive for validating disease correlations of panels. Seventy proteins can all be measured in a single sample of plasma, but the commercial cost using individual assays is $10,896.30. Thus in the end, the success of multi-analyte diagnostics is as much a matter of cost as science.

Mass spectrometry (MS) has solved the problem of identifying proteins resolved by 2D gel and other methods, and appears poised to provide general solutions to the analysis of complex protein mixtures as well. In the latter category, two general classes of approach can be distinguished: first, the "unbiased" discovery of proteins and peptides achieved via their detection or identification in a sample, and, second, the quantitative measurement of protein or peptides, usually requiring some type of additional standardization.

The power of mass spectrometry techniques to discover proteins in complex samples relies, with one notable exception described below, upon the existence of large protein sequence databases generally derived from DNA sequencing efforts. Since these databases are becoming comprehensive, the approach offers, at least in theory, a general solution to protein discovery. So far MS efforts have examined three basic windows into the proteome problem: whole proteins, peptide fragments obtained by digesting proteins in vitro (e.g., with trypsin), and naturally occurring peptides (the low molecular weight proteome, or peptidome).

Whole proteins can be analyzed by an approach termed SELDI-TOF (for surface-enhanced laser desorption ionization-time of flight) mass spectrometry, a variant of MALDI-TOF (matrix-enhanced laser desorption ionization-time of flight), in which chemical fractionation based on protein affinity for derivatized MS targets is used to reduce sample complexity to a level at which whole-protein MS can resolve a series of individual peaks. A significant disadvantage of the approach is that MS analysis of whole proteins does not directly provide a sequence-based identification (there being many proteins with close to a given mass), and hence the protein peaks discovered as markers are not strictly-speaking identified without significant additional effort. In particular, without a discrete identification, it is not generally possible to demonstrate that a peak is one protein analyte, or to translate the measurement into a classical immunoassay format. However, as has been clearly demonstrated by the success of some monoclonal antibody-based assays in which the target protein was unidentified, this does not pose a significant limitation to clinical use if the technology allows the analysis to be repeated in any interested laboratory (an effort which now appears to be underway).

A more general approach involves digesting proteins (e.g., with trypsin) into peptides that can be further fragmented (MS/MS) in a mass spectrometer to generate a sequence-based identification. The approach can be used with either electrospray (ESI) or MALDI ionization, and is typically applied after one or more dimensions of chromatographic fractionation to reduce the complexity of peptides introduced into the MS at any given instant. Optimized systems of multidimensional chromatography, ionization, mass spectrometry and data analysis (e.g., the multidimensional protein identification technology, or "MudPIT" approach of Yates, also referred to as shotgun proteomics) have been shown to be capable of detecting and identifying ~1,500 yeast proteins in one analysis (Washburn, Wolters, and Yates, *Nat Biotechnol* 19:242-7, 2001), while a single dimensional LC separation, combined with the extremely high resolution of a fourier-transform ion cyclotron resonance (FTICR) MS identified more than 1,900 protein products of distinct open reading frames (i.e., predicted proteins) in a bacterium. In human urine, a sample much more like plasma than the microbial samples mentioned above, Patterson used a single LC separation ahead of ESI-MS/MS to detect 751 sequences derived from 124 different gene products. Very recently, Adkins et al have used two chromatographic separations with MS to identify a total of 490 different proteins in human serum (Adkins and et al, *Molec Cell Proteomics* 1:947-955 (22002)), thus substantially expanding the proteome. Such methods should have the ability to deal with the numerous post-translational modifications characteristic of many proteins in plasma, as demonstrated by the ability to characterize the very complex post-translational modifications occurring in aging human lens.

Naturally-occurring peptides, typically below the kidney filtration cutoff and hence usually collected from urine or from blood hemodialysate, provide a complementary picture of many events at the low-mass end of the plasma proteome. Thousands of liters of human hemodialysate can be collected from patients with end stage renal disease undergoing therapeutic dialysis (Schepky, Bensch, Schulz-Knappe, and Forssmann, *Biomed Chromatogr* 8:90-4, 1994), and even though it contains only 50 ug/ml of protein/peptide material, it provides a large-scale source of proteins and peptides below 45 kd. Such material has been analyzed by combined chromatography and MS approaches to resolve approximately 5,000 different peptides, including fragments of 75 different proteins. Fifty-five percent of the fragments were derived from plasma proteins and 7% of the entries represented peptide hormones, growth factors and cytokines.

The protein discovery methods described above focus on identifying peptides and proteins in complex samples, but they generally offer poor quantitative precision and reproducibility. The well-known idiosyncrasies of peptide ionization arise in large part because the presence of one peptide can affect the ionization and, thus, signal intensity of another. These have been major impediments to accurate quantitation by mass spectrometry. This problem can be overcome, however, through the use of stable isotope-labeled internal standards. At least four suitable isotopes ($^{2}H$, $^{13}C$, $^{15}N$, $^{18}O$) are commercially available in suitable highly enriched (>98 atom %) forms. In principle, abundance data as accurate as that obtained in MS measurement of drug metabolites with internal standards (coefficients of variation<1%) should ultimately be obtainable. In the early 1980's $^{18}O$-labeled enkephalins were prepared and used to measure these peptides in tissues at ppb levels. In the 1990's GC/MS methods were developed to precisely quantitate stable isotope-labeled amino acids, and hence protein turnover, in human muscle and plasma proteins labeled in vivo. The extreme sensitivity and precision of these methods suggested that stable isotope approaches could be applied in quantitative proteomics investigations, given suitable protein or peptide labeling schemes.

Over the past three years, a variety of such labeling strategies have been developed. The most straightforward approach (incorporation of label to a high substitution level during biosynthesis), has been successfully applied to microorganisms (Lahm and Langen, *Electrophoresis* 21:2105-14, 2000; Oda, Huang, Cross, Cowburn, and Chait, *Proc Natl Acad Sci USA* 96:6591-6, 1999) and mammalian cells in culture, but is unlikely to be usable directly in humans for cost and ethical reasons. A related approach (which is applicable to human proteins) is the now-conventional chemical synthesis of monitor peptides containing heavy isotopes at specific positions. Post-synthetic methods have also been developed for labeling of peptides to distinguish those derived from an "internal control" sample from those derived from an experimental sample, with a labled/unlabeled pair subsequently being mixed and analyzed together by MS. These methods include Aebersold's isotope-coded affinity tag (ICAT) approach, as well as deuterated acrylamide and N for labeling peptide sulfhydrals, deuterated acetate to label primary amino groups, n-terminal-specific reagents, permethyl esterification of peptides carboxyl groups, and addition of twin $^{18}O$ labels to the c-terminus of tryptic peptides during cleavage.

Small amounts of proteins such as tissue leakage proteins are important because a serious pathology can be detected in a small volume of tissue by measuring release into plasma of a high-abundance tissue protein. Cardiac myoglobin (Mb) is present in plasma from normal subjects at 1-85 ng/mL, but is increased to 200-1,100 ng/mL by a myocardial infarction, and up to 3,000 ng/mL by fibrinolytic therapy to treat the infarct. Cytokines, which in general act locally (at the site of infection or inflammation), are probably not active at their normal plasma concentrations (or even at the higher levels pertaining after a major local release) because they are diluted from uL or mL volumes of tissue into 17 L of interstitial fluid. Hence they are in a sense leakage markers as well, though their presence in plasma does not indicate cell breakage. A commercially useful process for making such measurements is an objective of the instant invention.

The original idea of combining stable isotope labeled peptide internal standards with an anti-peptide-antibody enrichment step to make a quantitative MS-based assay for a peptide was published in 1989 by Jardine et al (Lisek, Bailey, Benson, Yaksh, and Jardine, *Rapid Commun Mass Spectrom* 3:43-6, 1989). The reference discloses use of a single synthetic stable isotope labeled peptide (substance P sequence) spiked into neuronal tissue, followed (after extraction from the tissue) by binding to an immobilized anti-substance-P-specific antibody, to enrich the neuropeptide substance P, and finally quantitation by MS. Substance P abundance was calculated from the ratio of natural peptide ion current to the internal labeled standard peptide of the same sequence: i.e., demonstrating all elements of the single analyte peptide standard/antibody enrichment process. Jardine et al used a 10-fold molar excess of the labeled version of substance P to act as both internal standard and carrier, and measured masses by fast-atom bombardment (FAB) selected-ion monitoring (SIM) MS. As reported, the Jardine approach was applied only to endogenous peptides, not in vitro prepared protein fragments (e.g., a tryptic digest of one or more larger proteins). The antibody capture was carried out offline, the eluent concentrated and then applied to a C18 capillary column from which it was eluted into the ESI source.

Nelson et al (Intrinsic Bioprobes) have developed similar methods for enriching specific proteins by use of Ab's, and then detecting by MS (with and without added isotope-labeled standards), though they do not mention application to peptides derived by digestion of target proteins. They did assay human beta-2 microglobulin using an antibody to enrich the protein from plasma, and using equine b2M (from added equine serum) as an internal calibrant (Kiernan, Tubbs, Nedelkov, Niederkofler, and Nelson, *Biochem Biophys Res Commun* 297:401, 2002; Niederkofler, Tubbs, Gruber, Nedelkov, Kiernan, Williams, and Nelson, *Anal Chem* 73:3294-9, 2001a). Nelson (U.S. Pat. No. 5,955,729) has used internal standard peptides added to samples of affinity purified natural peptides, but in this case the standard peptides were of different sequence from the analytes and were not bound on the same antibodies. Both the stable isotope labeled peptides and anti-peptide antibodies are now commonplace reagents, available from multiple commercial sources.

Since 1995 a single peptide has been used as a surrogate for the presence of a parent protein (from which the peptide was derived by proteolytic digestion) in a complex protein mixture, based on, e.g., MALDI-PSD (Griffin, MacCoss, Eng, Blevins, Aaronson, and Yates, *Rapid Commun Mass Spectrom* 9:1546-51, 1995) or ion trap (Yates, Eng, McCormack, and Schieltz, *Anal Chem* 67:1426-36, 1995) MS/MS spectra.

Regnier et al have pursued a "signature peptide" quantitation approach (Chakraborty and Regnier, *J Chromatogr A* 949:173-84, 2002a; Chakraborty and Regnier, *J Chromatogr A* 949:173-84, 2002a; Zhang, Sioma, Wang, and Regnier, *Anal Chem* 73:5142-9, 2001a), also the subject of a published patent application (Regnier, F. E., X. Zhang, et al. US 2002/ 0037532), in which protein samples are digested to peptides by an enzyme, differentially labeled with isotopically different versions of a protein reactive agent, purified by means of a selective enrichment column, and combined for MS analysis using MALDI or ESI-MS. This method includes some of the features of the present invention, but specifically elects to use post-synthetic labeling of peptides in digests to generate the internal standards (to allow analysis of unknown peptides), and describes the application of antibodies as one of the means for enriching for group-specific characteristics of peptides rather than unique peptides: "A portion of the protein or peptide amino acid sequence that defines an antigen can also serve as an endogenous affinity ligand, which is particularly useful if the endogenous amino acid sequence is common to more than one protein in the original mixture. In that case, a polyclonal or monoclonal antibody that selects for families of polypeptides that contain the endogenous antigenic sequence can be used as the capture moiety" (Regnier, F. E., X. Zhang, et al. US 2002/0037532).

Scrivener, Barry et al (Scrivener, Barry, Platt, Calvert, Masih, Hextall, Soloviev, and Terrett, *Proteomics* 3:122-128, 2003; Barry et al, U.S. patent application 2002/0055186) have used antibodies fixed on an array to enrich peptides from a digest for detection by MALDI MS. This approach requires that the antibodies be fixed in a particular spatial form convenient for MALDI MS analysis (generally an array on the surface of a planar substrate), and does not include labeled versions of target peptides as internal standards for quantitation.

Gygi used stable-isotope-labeled synthetic peptides to quantitate the level of phosphorylated vs non-phosphorylated peptides in the digest of a protein isolated on a 1-D gel (Stemmann, Zou, Gerber, Gygi, and Kirschner, *Cell* 107:715-26, 2001) and has described a method for peptide quantitation (WO03016861) that uses the approach of Jardine with the addition of greater mass spectrometer resolution (selected reaction monitoring [SRM] in which the desired peptide is isolated by a first mass analyzer, the peptide is fragmented in flight, and a specific fragment is detected using a second mass analyzer). Conventional separations (eg., reverse phase LC) rather than specific capture reagents (such as antibodies) were to separate peptides prior to MS.

Standards can be made by chemical synthesis. Crowther published a similar approach in 1994 (*Anal Chem* 66:2356-61, 1994) to detect peptide drugs in plasma using deuterated synthetic internal standards. Rose used synthetic stable isotope labeled insulin to standardize an MS method for quantitation of insulin (a small protein or large peptide), in which the spiked sample was separated by reverse phase chromatography to fractionate the sample Even larger proteins can now be made by total chemical synthesis.

Several means for affinity capturing of proteins and peptides using antibodies are known to the art. Antibody-bound proteins have beeen digested to eliminate non-epitope peptides, followed by elution and identification of the epitope peptide by MS (*Proc Natl Acad Sci USA* 87:9848-52, 1990). DNA has been used (not an Ab) to bind lactoferrin in infant urine for analysis by MS (*Pediatr Res* 29:243-50, 1991).

Protein:protein interactions have previously been mapped by capturing epitope peptides on an antibody, followed by MS (*Methods Mol Biol* 146:439-52, 2000). Methods have been developed for identifying peptide epitopes by allowing an immobilized Ab to subtract the binding (epitope) peptide from a digest prior to MS (*J Am Soc Mass Spectrom* 11:746-50, 2000).

An antibody on magnetic beads has been used to bind a selected protein, which was then digested and the peptides analyzed by MS (*J Am Soc Mass Spectrom* 9:208-15, 1998). Hurst developed a method for solid phase antibody affinity capture of a protein ligand (TNF-alpha) and subsequent analysis by MS (*Anal Chem* 71:4727-33, 1999). Wehland has enriched peptides by binding to antibodies and other proteins to identify linear binding epitopes (*Anal Biochem* 275:162-70, 1999).

Naylor developed a similar procedure for isolating transferrin prior to MS for the detection of glycosylation variants (*Anal Biochem* 296:122-9, 2001). Clarke and Naylor published (Clarke, Crow, Younkin, and Naylor, *Anal Biochem* 298:32-9, 2001) a method in which the 40 amino acid amyloid beta peptide is captured by an antibody to 16 amino acids, eluted and quantitatively detected by MS. The method did not include use of an internal standard labeled with stable isotopes.

Thibault used a microfluidic device to capture c-myc peptides on antibodies prior to MS, providing detection of spiked peptide to 20 ng/ml (*Mol Cell Proteomics* 1:157-68, 2002).

Recycling immunoaffinity, using immobilized polyclonal antibody columns, has been known since 1975. Using antibodies immobilized on CNBr-activated Sepharose or commercially available POROS supports (Applied Biosystems), polyclonal antibodies have been shown to be recyclable several hundred times without loss of substantial specific binding capacity.

The instant invention uses several of the cited methods of the prior art in an entirely different combination. In the descriptions that follow, quantitation of proteins, peptides and other biomolecules is addressed in a general sense, and hence the invention disclosed is in no way limited to the analysis of plasma and other body fluids.

SUMMARY OF THE INVENTION

The instant invention provides an economical flow-through method for determining amount of target proteins in a sample. An antibody preparation (whether polyclonal or monoclonal, or any equivalent specific binding agent) is used to capture and thus enrich a specific monitor peptide (a specific peptide fragment of a protein to be quantitated in a proteolytic digest of a complex protein sample) and an internal standard peptide (the same chemical structure but including stable isotope labels). Upon elution into a suitable mass spectrometer, the natural (sample derived) and internal standard (isotope labeled) peptides are quantitated, and their measured abundance ratio used to calculate the abundance of the monitor peptide, and its parent protein, in the initial sample. This is different from the use of a less-specific affinity method to capture a class of monitor peptides that share a property such as glycosylation, inclusion of a cysteine or a lysine residue, phosphorylation; or use of another form of fractionation that selects analytes residing in a specific cell fraction, having a similar native molecular mass (e.g., size exclusion chromatography), charge, etc. Such class-specific fractionation approaches has been exploited by others including Regnier, where the objective and practice is to reduce the complexity of the mixture presented to the MS somewhat, so as not to overwhelm its resolution and sensitivity, but not to a single peptide per affinity binding agent (usually antibody). In the present invention, the objective is to select, with a given antibody or other binding agent, a single peptide derived from a single target protein (or other analyte) from the digest of a complex protein sample. The invention provides methods for multiplexing peptide measurements, for effectively selecting monitor peptides sequences, and for further increasing measurement sensitivity.

This disclosure also teaches supports with binding agents which can collect from a sample target peptides and proteins of varying concentration. By selective use of binding agents and amounts of such agents, it is possible to obtain a large portion of the target peptides/proteins which are in small quantities in the sample, while binding only a small portion of target peptides/proteins which are in high concentration in the sample. This improved method facilitates the efficiency and accuracy of MS reading by narrowing the range of concentration of the target proteins or peptides in the elute introduced into the spectrometer.

BRIEF DESCRIPTION OF THE DRAWINGS

FIG. 1 illustrates the fluting of the antibody-containing holes or tubes to increase surface area.

FIG. 5. In use, as shown in FIG. 5, disc 39 is held as 40 between clear discs 41 and 42, containing aligned holes. The arrangement keeps discs 41 and 42 stationary while disc 40 can be rotated by engagement of external means with the teeth 9.

FIG. 6. The operation of the system in one analytical cycle is shown in FIG. 6, where disc 63 with teeth 64 contains sixteen antibody-containing holes 65 and four clear holes 70-73.

FIG. 6b is a circular cross-section through the disks shown in FIG. 6.

FIG. 7 indicates how the entire system in integrated, with the mass spectrometer 74 attached to disc analyzer 75, in turn fed discs made and controlled by 76, all under the control of computer 77.

DETAILED DESCRIPTION OF THE INVENTION

Figure 1:
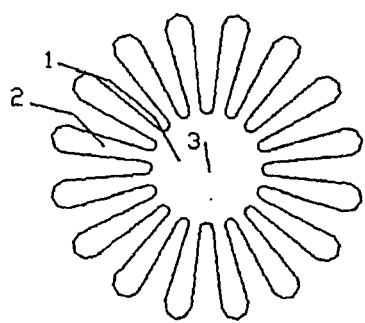
FIG. 1. Each antibody binding surface comprises the lumen of a hole in a plate (here a circular plate), and the lumen's surface area is increased by fluting.

This invention provides a flow-through process for identifying and quantitating peptides and/or proteins in a sample. While many of the methods disclosed above are incorporated into the methods of the invention, the process for such a commercially useful process had not previously been disclosed.

The invention is illustrated using the methods to detect protein analytes through use of monitor peptides and anti-peptide antibodies, although other sets of reagents can be used to similarly detect other classes of analyte molecules. Throughout the disclosure, the terms "analyte", and "ligand" may be any of a variety of different molecules, or components, pieces, fragments or sections of different molecules that one desires to measure or quantitiate in a sample. The term "monitor fragment" may mean any piece of an analyte up to and including the whole analyte which can be produced by a reproducible fragmentation process (or without a fragmentation if the monitor fragment is the whole analyte) and whose abundance or concentration can be used as a surrogate for the abundance or concentration of the analyte. The term "monitor peptide" means a peptide chosen as a monitor fragment of a protein or peptide.

The terms "binding agent" and "receptor" may be any of a large number of different molecules, biological cells or aggregates, and the terms are used interchangeably. In this context, a binding agent binds to an analyte being detected in order to enrich it prior to detection, and does so in a specific manner, such that only a single analyte is bound and enriched. Proteins, polypeptides, peptides, nucleic acids (oligonucleotides and polynucleotides), antibodies, ligands, polysaccharides, microorganisms, receptors, antibiotics, test compounds (particularly those produced by combinatorial chemistry) may each be a binding agent.

The term "antibody" may be any of the classes of immunoglobulin molecules of any species, or any molecules derived therefrom, or any other specific binding agents constructed by variation of a conserved molecular scaffold so as to specifically bind an analyte or monitor fragment. The term "anti-peptide antibody" may be any type of antibody (in the preceding general sense) that binds a specific peptide, monitor peptide, or other monitor fragment for the purposes of enrichment from a sample or processed sample. In general, any use made of an antibody herein is understood to be a purpose that could also be served by a binding agent as defined above.

The term "bind" includes any physical attachment or close association, which may be permanent or temporary. Generally, reversible binding includes aspects of charge interactions, hydrogen bonding, hydrophobic forces, van der Waals forces. etc., that facilitate physical attachment between the molecule of interest and the analyte being measured. The "binding" interaction may be brief as in the situation where binding causes a chemical reaction to occur. Reactions resulting from contact between the binding agent and the analyte are also within the definition of binding for the purposes of the present invention, provided they can be later reversed to release a monitor fragment.

The terms "internal standard", "isotope-labeled monitor fragment", or "isotope-labeled monitor peptide" may be any altered version of the respective monitor fragment or monitor peptide that is 1) recognized as equivalent to the monitor fragment or monitor peptide by the appropriate binding agent and 2) differs from it in a manner that can be distinguished by a mass spectrometer, either through direct measurement of molecular mass or through mass measurement of fragments (e.g., through MS/MS analysis), or by another equivalent means.

The term "specific monitor peptide" refers to a peptide having a unique sequence in the region of antibody (or other binding agent) contact, and derived from the protein product of a single gene. Peptides having non-material modifications of this sequence, such as a single amino acid substitution (as may occur in natural genetic polymorphisms), substitutions outside the region of contact or chemical modifications to the peptide (including glycosylation, phosphorylation, and other well-known post-translational modifications) that do not materially affect binding are included in this term. Each antibody preparation (or other binding agent) is meant to enrich a single monitor peptide to serve as the surrogate to a single protein analyte. In order to detect and quantitatively measure protein analytes, the invention makes use of anti-peptide antibodies (or any other binding entity that can reversibly bind a specific peptide sequence of about 5-20 residues) to capture specific peptides from a mixture of peptides, such as that arising, for example, from the specific cleavage of a protein mixture (like human serum) by a proteolytic enzyme such as trypsin or a chemical reagent such as cyanogen bromide. By capturing a specific peptide through binding to an antibody (the antibody being typically coupled to a solid support), followed by washing of the antibody:peptide complex, and finally elution of the bound peptide into a small volume (typically achieved by an acid solution such as 10% acetic acid), the invention makes it possible to enrich specific peptides that may be present at low concentrations in the whole digest, and therefore undetectable in simple mass spectrometry (MS) or liquid chromatography-MS (LC/MS) systems against the background of more abundant peptides present in the mixture. This enrichment step is intended to capture peptides of high, medium or low abundance and present them for MS analysis: it therefore discards information as to the relative abundance of a peptide in the starting mixture in order to boost detection sensitivity. This abundance information, which is of great value in the field of proteomics, can be recovered, however, through the use of isotope dilution methods: the invention makes use of such methods (preferably using stable isotopes) in combination with specific peptide enrichment, to provide a method for quantitative analysis of peptides, including low-abundance peptides.

The approach is to create a version of the peptide to be measured which incorporates one or more isotopes of mass different from the predominant natural isotope, thus forming a labeled peptide variant that is chemically identical (or nearly-identical) to the natural peptide present in the mixture, but is nevertheless distinguishable by a mass spectrometer because of its altered peptide mass (the isotopic label). The preferred method for creating the labeled peptide is chemical synthesis, wherein a peptide identical to the natural one can be made by incorporating amino acid precursors that contain heavy isotopes of hydrogen, carbon, oxygen or nitrogen to introduce the isotopic label. This isotopic peptide variant is used as an internal standard, added to the sample peptide mixture at a known concentration before enrichment by antibody capture. The antibody thus captures and enriches both the natural and the labeled peptide together (having no differential affinity for either since they are chemically the same) according to their relative abundances in the sample. Since the labeled peptide is added at a known concentration, the ratio between the amounts of the natural and labeled forms detected by the final MS analysis allows the concentration of the natural peptide in the sample mixture to be calculated. Thus the invention makes it possible to measure the quantity of a peptide of low abundance in a complex mixture, and since the peptide is typically produced by quantitative (complete) cleavage of a mixture of proteins, the abundance of the parent protein in the mixture of proteins can be deduced. The invention can be extended to cover multiple peptides measured in parallel, and can be automated through computer control to afford a general system for protein measurement. Creating a new protein-specific assay thus requires only that a peptide-specific antibody and a labeled peptide analog be created. A key feature of the invention is that it is directed at establishing quantitative assays for specific proteins selected a priori, rather than at the problem of comparing all of the unknown components of two or more samples to one another. It is this focus on specific assays that makes it attractive to generate specific antibodies to each monitor peptide (in principle one antibody binding one peptide for each assay): it is currently unattractive to create the thousands to millions of possible anti-peptide antibodies that would be required to cover the entire range of possible human proteins, for example. Previously described methods have not focused on anti-peptide antibodies for this reason, but used instead general affinity concepts that would bind and enrich all of a class of peptides by recognizing a ligand, label or feature common to the class: e.g., immobilized metal affinity chromatography (IMAC) to select phosphopeptides as a group, anti-phosphotyrosine antibodies to select anti-phosphotyrosine-containing peptides as a group, or lectins to select glycopeptides as a group. The objective of this invention is to provide means to enrich each peptide sequence specifically with a different antibody (or other equivalently selective binding reagent).

A further objective is to deliver a series of different monitor peptides (selected by a corresponding series of specific antibodies) to a mass spectrometer at very nearly the same abundance and free of other extraneous peptides. By equalizing the abundance of a series of peptides, the method ensures that all the peptides are within the mass spectrometer's dynamic range and that this dynamic range can be optimally employed in spanning the true dynamic range of the peptide analytes. If the MS system has a dynamic range of 1000 (a range of 100 to 10,000 is typical depending on the type of MS), the method ensures that all of the peptides are presented to the MS at a level in the middle of that range, thus allowing an optimal capacity to detect increases or decreases in relative abundance of the natural and isotopically labeled forms. If the peptides were presented to the MS at different abundances (e.g., at relative concentrations of 1, 0.001 and 1,000), then the MS will have great difficulty in detecting equivalent quantitative differences between natural and isotopically labeled forms of these three peptides. By "flattening" the abundance distribution of the peptides, the mass spectrometer's quantitative resolution is substantially enhanced.

While some skill will be useful in the selection of the optimal peptide(s) for monitoring each protein, the approach is general and inexpensive relative to the substantial cost of creating the high-affinity antibodies and other elements required to perform a typical sandwich-type quantitative immunoassay. It may compete with low-volume immunoassay technologies as a means of measuring tens to hundreds of specific proteins in mixtures such as human blood serum and plasma.

The preferred embodiment combines 1) existing methods for creation and affinity purification of antibodies that tightly but reversibly bind short peptide sequences; 2) existing methods for digestion of complex protein mixtures to yield short peptides; 3) existing methods for synthesis of defined peptides containing isotopic labels; 4) existing methods for efficient recycling affinity chromatography to repeatedly capture and deliver peptides; and 5) existing methods for MS measurement of ratios of labeled and unlabeled (sample-derived) peptides to yield a quantitative measurement. Herein is described the combined method, using plasma proteins as an example. In addition to combining the individual steps in a novel way, we describe novel methods of multiplexing and automating such assays, and ways of optimizing the choice of monitor peptide sequences. The application to any other protein or peptide mixture will be obvious to a person skilled in the art. The use of peptide-binding agents other than antibodies (e.g., RNA aptamers, peptide aptamers, etc.) will also be obvious to a person skilled in the art. Likewise the generalization of the concept to the quantitative detection of other biomolecules, such as nucleic acids and oligosaccharides, or to any molecular entity that can be 1) produced in an isotopically labeled form and 2) to which a reversible biding agent can be created, will be obvious.

Single Analyte Embodiment (1:)

In the simplest embodiment, the following steps are carried out for each protein one wishes to measure in plasma in order to generate a specific quantitative assay system. The starting point is a protein identification, typically expressed as an accession number in a sequence database such as SwissProt or Genbank. The steps are:

Select Monitor Peptide (Step a)

Using the known sequence of the protein, one selects one or more peptide segments within it as "monitor peptides". A good monitor peptide is defined by a set of criteria designed to select peptides that can be chemically synthesized with high yield, that can be detected quantitatively in an appropriate mass spectrometer, and that elicit antibodies when used as antigens, although any peptide resulting from cleavage with the desired enzyme is a possible choice. One useful set of criteria is the following:

1: The peptide has a sequence that results from cleavage of the protein with a desired proteolytic enzyme (e.g., trypsin). All the candidate tryptic peptides can be easily computed from the protein sequence by application of generally available software.

2: The peptide should be hydrophilic overall, and soluble in conventional solvents used in enzymatic digestion and affinity chromatography. Hydrophilic peptides can be selected based on computed scores obtained for each peptide from generally available software programs. In general the hydrophilic peptides are those that contain more polar amino acids (his, lys, arg, glu, asp) and fewer hydrophobic amino acids (trp, phe, val, leu, ile).

3: The peptide should preferably contain no cys, as a c-terminal cys may be added for convenience in conjugation of the immunogen, and the presence of two cys in a peptide can lead to undesirable dimerization and cross-linking.

4: the peptide should ionize well by either electrospray (ESI) or matrix-assisted laser desorption (MALDI) ionization. This characteristic can be estimate by software programs or determined experimentally by MS analysis of a digest of the protein in question to see which peptides are detected at highest relative abundance.

5: The peptide should be immunogenic in the species in which the antibody will be raised. Immunogenicity is generally better for peptides that are hydrophilic (compatible with (2) above); that include a bend predicted by secondary structure prediction software; that include no glycosylation sites; and that are 10-20 amino acids in length.

6: The peptide should not include within it the sites of any common sequence polymorphisms (i.e., genetic variants) in the target protein (as this could affect the estimation of the respective protein's abundance if the variant peptide does not appear at the expected mass).

7: the peptide should not share appreciable homology with any other protein of the target organism (as determined for example by the BLAST sequence comparison program). This characteristic should tend to reduce any interference in the antibody capture step from peptides originating in proteins other than the target.

All possible peptides derived from the target protein can easily be evaluated according to these criteria and one or more peptides selected that best balance the requirements of the method. Specifically it is straightforward to create a database of all the peptides and their derived properties for a finite set of analytes such as the known proteins in plasma, and to use this database as a basis for selection of monitor peptides. Beginning with the known amino acid sequences of protein analytes, efficient algorithms can construct all the possible tryptic peptides that will be created by trypsin digestion of the protein. These tryptic peptide sequences can be stored as records in a database, and similar records generated for other possible cleavage enzymes and reagents. Additional algorithms can be employed to compute various physical and biological properties of each peptide, including length, mass, net charge at neutral pH, propensity to adopt secondary structure, hydrophilicity, etc. These derived data can be tabulated for each peptide, and additional aggregate calculations performed to develop prioritizing scores associated with likelihood of success as a monitor peptide. These priority scores can be sorted to select preferred candidate monitor peptides for each protein.

It is also possible to add experimental data to the prioritization. It is possible, for example, to generate by synthesis all the individual tryptic peptide sequences derived from a protein, and to immobilize these peptides in an array on a membrane. Such as array can then be probed with an antibody to the whole protein, or with a mixture of antibodies raised against a mixture of proteins including the target protein, and the binding of antibody to the various peptides revealed and quantitated by secondary staining with a second antibody labeled so as to be detectable by luminescence, fluorescence, or colorimetric staining (the PEPSCAN approach {Carter *Methods Mol Biol* 36: 207-223 (1994). Those peptides situated where antibody binding is detected are thus shown to be capable of eliciting and antibody response. The major limitation to thus using PEPSCAN is the requirement for an existing antibody to the protein of choice, or to a mixture containing it. Such an antibody may be available when the protein is one that has been studied before, or it may be generated in conjunction with an attempt to select the optimal monitor peptide.

Creating Isotope Monitor Peptides (Step b)

An isotopically labeled version of the selected peptide(s) is then made in which the chemical structure is maintained, but one or more atoms are substituted with an isotope such that an MS can distinguish the labeled peptide from the normal peptide (containing the natural abundance of each elements' isotopes). For example, nitrogen-15 could be introduced instead of the natural nitrogen-14 at one or more positions in the synthesized peptide. The synthesized peptide will be heavier by a number of atomic mass units equal to the number of substituted nitrogens. The peptide is carefully made so that the number of added mass units is known and well-determined (i.e., all of the material produced as one standard has the same mass insofar as possible—achieved by using highly enriched isotopic variants of the amino acids, for example). In the preferred embodiment, nitrogen-15 labeled amino acid precursors substituted at >98% are used at one or more positions in the peptide synthesis process to introduce between 4 and 10 additional mass units compared to the natural peptide. Such nitrogen-15 labeled amino acid precursors (or their carbon-13 labeled equivalents) are commercially available as FMOC derivatives suitable for use directly in conventional commercial peptide synthesis machines. The resulting labeled monitor peptides are purified using conventional LC methods (typically to >90% purity) and characterized by MS to ensure the correct sequence and mass.

Creating Anti-Peptide Antibodies (Step c)

To immunize an animal for production of anti-peptide antibodies, the same peptide (labeled or not, if this is, as expected, more economical) is coupled to a carrier protein (e.g., keyhole limpet hemocyanine (KLH); not homologous to a human protein) and used to immunize an animal (such as a rabbit, chicken, goat or sheep) by one of the known protocols that efficiently generate anti-peptide antibodies. For convenience, the peptide used for immunization and antibody purification preferably contains additional c-terminal residues added to the monitor peptide sequence (here abbreviated MONITOR), e.g.: nterm-MONITOR-lys-gly-ser-gly-cys-cterm. The resulting extended monitor peptide can be conveniently coupled to carrier KLH that has been previously reacted with a heterobifunctional reagent such that multiple SH-reactive groups are attached to the carrier. In classical immunization with the peptide (now as a hapten on the carrier protein), a polyclonal antiserum will be produced containing antibodies directed to the peptide, to the carrier, and to other non-specific epitopes. Alternatively, there are many methods known in the art for coupling a peptide, with or without any extensions or modifications, to a carrier for antibody production, and any of these may be used. Likewise there are known methods for producing anti-peptide antibodies by means other than immunizing an animal with the peptide on a carrier. Any of the alternatives can be used provided that a suitable specific reversible binding agent for the monitor peptide is produced.

Specific anti-peptide antibodies are then prepared from this antiserum by affinity purification on a column containing tightly-bound peptide. Such a column can be easily prepared by reacting an aliquot of the extended monitor peptide with a thiol-reactive solid support such as commercially available thiopropyl Sepharose. Crude antiserum can be applied to this column, which is then washed and finally exposed to 10% acetic acid (or other elution buffer of low pH, high pH, or high chaotrope concentration) to specifically elute antipeptide antibodies. These antibodies are neutralized or separated from the elution buffer (to prevent denaturation), and the column is recycled to physiological conditions for application of more antiserum if needed.

The peptide-specific antibody is finally immobilized on a column, bead or other surface for use as a peptide-specific affinity capture reagent. In the preferred embodiment, the anti-peptide antibody is immobilized on commercially available protein A-derivatized POROS chromatography media (Applied Biosystems) and covalently fixed on this support by covalent crosslinking with dimethyl pimelimidate according to the manufacturer's instructions. The resulting solid phase media can bind the monitor peptide specifically from a peptide mixture (e.g., a tryptic digest of serum or plasma) and, following a wash step, release the monitor peptide under mild elution conditions (e.g., 10% acetic acid). Restoring the column to neutral pH then regenerates the column for use again on another sample, a process that is well known in the art to be repeatable hundreds of times.

The preferred affinity of the anti-peptide antibodies is in the range of 100 to 100,000,000. A higher affinity is required to enrich lower abundance peptides, i.e., to capture peptides at low concentration.

Digestion of Sample to Peptides (Step d)

A sample of plasma, in which one wishes to measure the selected protein, is digested essentially to completion with the appropriate protease (in this case trypsin) to yield peptides (including the monitor peptide selected in step 1). For a monitor peptide whose sequence appears once in the target protein sequence, this digestion should generate the same number of monitor peptide molecules as there were target protein molecules in the stating sample. The digestion is carried out by first denaturing the protein sample (e.g., with urea or guanidine HCl), reducing the disulfide bonds in the proteins (e.g., with dithiothreitol or mercaptoethanol), alkylating the cysteines (e.g., by addition of iodoacetamide), quenching excess iodoacetamide by addition of more dithiothreitol or mercaptoethanol, and finally (after removal or dilution of the denaturant) addition of the selected proteolytic enzyme (e.g. trypsin), followed by incubation to allow digestion. Following incubation, the action of trypsin is terminated, either by addition of a chemical inhibitor (e.g., DFP or PMSF) or by denaturation (through heat or addition of denaturants, or both) or removal (if the trypsin is on a solid support) of the trypsin. The destruction of the trypsin activity is important in order to avoid damage to antibodies later by residual proteolytic activity in the sample.

Adding Isotopically-Labeled Monitor Peptide Internal Standards (Step e)

A measured aliquot of isotopically-labeled synthetic monitor peptide is then added to a measured aliquot of the digested sample peptide mixture in an amount close to or greater than (if the standard serves as carrier for a low abundance peptide) the expected abundance of the same "natural" peptide in the sample aliquot. Following this addition the monitor peptide will be present in the sample in two forms (natural and isotopically-labeled). The concentration of the isotopically-labeled version is accurately known based on the amount added and the known aliquot volumes.

Enrichment of the Monitor Peptide by Antibody Capture and Elution (Step f)

The peptide mixture (digest with added isotopically-labeled monitor peptides) is exposed to the peptide-specific affinity capture reagent, which preferentially binds the monitor peptide but does not distinguish between labeled and unlabeled forms (since isotopic substitutions are not expected to affect antibody binding affinity). Following a wash step (e.g., phosphate-buffered saline) the bound peptides are then eluted (e.g., with 10% acetic acid, or with a mixture of water and acetonitrile), for MS analysis. The affinity support can, if desired, be recycled in preparation for another sample. In the high-throughput assay applications envisioned, it will be advantageous to recycle the immobilized antibody binding hundreds, if not thousands, of times. Current evidence indicates that rabbit polyclonal antibodies can be recycled at least 200 times when antigens are eluted with 5% or 10% acetic acid and total exposure to acid is kept short (e.g., less than 1 minute before regeneration with neutral pH buffer). In a capillary column format, where the immobilized antibody bed can be submicroliter in size, the duration of acid exposure could be further decreased, possibly extending the life of the immobilized antibody adsorbent even further.

The efficiency of peptide capture is governed by the affinity constant of the antibody for the peptide and by the concentrations of both peptide and antibody. We are concerned particularly with the fraction of peptide that is combined with antibody. The relevant general equations are:

$$Ab+Pep=AbPep,$$

$$K_a=[AbPep]/([Ab]\times[Pep])$$

$$K_a \times [Ab]=[AbPep]/[Pep]$$

[Ab], [Pep] and [AbPep] are the concentrations of Ab, Pep, AbPep, respectively; and $K_a$ is the affinity constant governing the binding reaction under the solution conditions given. In the present embodiment we are concerned particularly with low abundance peptides (since high abundance peptides will be relatively easy to capture), and thus we arrange that the antibody is present at the maximum concentration obtainable on the solid support ([Ab]=approximately $10^{-5}$ M for IgG bound to Protein A derivatized POROS resin). Since at this concentration 100 fmol of Ab occupies only 1 nL of POROS, and since the columns actually used, though very small by conventional standards, are much larger than this, the antibody will be present in substantial excess over the peptide, and we can assume any attainable level of [AbPep] will not significantly decrease [Ab], which can be assumed to be constant ($10^{-5}$ M). Typical antipeptide antibodies have affinity constants in the range $10^6$-$10^8$. Hence the ratio of amount of antibody-bound peptide to free peptide ([AbPep]/[Pep]) is given by $K_a \times [Ab] = 10^6$-$10^8 \times 10^{-5} = 10$ to $10^3$. A majority (90%) of peptide should thus be bound to antibody even with a relatively low affinity ($K_a=10^6$) antibody, while a high affinty antibody gives 99.9% antibody binding. This ratio is independent of the antibody's concentration: the antibody captures whatever peptide is available, and the sensitivity is determined primarily by the detector's sensitivity.

The above calculations apply to equilibrium binding. The affinity constant $K_a$ is the quotient of the "on-rate" $K_{on}$ and the "off-rate" $K_{off}$ ($K_a=K_{on}/K_{off}$). $K_n$ is similar for all peptide-antibody binding reactions since it is determined mainly by diffusion (the molecules bumping into one another). The typical value of $K_n$ is $10^5$ to $10^6$ $M^{-1}$ $sec^{-1}$, and here we assume the more conservative value ($10^6$). From this and the typical values of $K_a$ used above ($10^6$-$10^8$) we can calculate the range of values for $K_{off}$: 1 to 0.01 per second, or in other works 1 to 100 seconds. If the peptide can rebind to another binding site after it comes off, then it will stay bound for another similar period. Thus it is likely that the peptide will stay on the column during loading and washing provided these are relatively fast and provided that there are excess binding sites (antibodies) for re-binding. Elution can be very fast because elution conditions (e.g., low pH) alter the peptide:antibody interaction and drastically increase the off rate. For this reason an antigen bound to an immobilized antibody column is observed to elute in a sharp frontal zone even during rapid recycling affinity chromatography. Such frontal behavior allows elution of captured peptide in a very small volume, particularly if the ratio of column length to diameter is large. This later requirement is met by a capillary immobilized antibody column having, e.g., diameter 100 microns and a length of 3 mm (length/diameter=30, volume=~25 nL). In such a column a peptide zone can be eluted in a 1 mm zone, having a volume of 8 nl. If the digest of a 10 uL plasma sample can be loaded on the column, the monitor peptide captured with high efficiency as described above, and then eluted in 8 nL, than the method of the invention achieves a concentration increase of 1,000-fold and simultaneously removes a large amount of potentially interfering peptide material.

The enrichment step is an important step of the method because it allows enrichment and concentration of low abundance peptides, derived from low abundance proteins in the sample. Ideally, this enrichment process delivers only the monitor peptide to the MS, and makes its detection a matter of absolute MS sensitivity, rather than a matter of detecting the monitor peptide against a background of many other, potentially much higher abundance peptides present in the whole sample digest. This approach effectively extends the detection sensitivity and dynamic range of the MS detector in the presence of other high abundance proteins and peptides in the sample and its digest.

Analysis of the Captured Monitor Peptides by MS (Set g)

The monitor peptide (including natural and isotopically-labeled versions) enriched in the preceding step is delivered into the inlet of a mass spectrometer, preferably by electrospray ionization. In a preferred embodiment, the peptide is introduced directly into the mass spectrometer in the elution buffer (e.g., 10% acetic acid). Alternatively the monitor peptide is applied to a reverse phase (e.g., C18) column and eluted by a gradient (e.g., of acetonitrile/trifluoroacetic acid in water) into an electrospray source of the mass spectrometer (i.e., LC/MS). The mass spectrometer can be an ion trap, a triple quadrupole, an ESI-TOF, a Q-TOF type instrument, or any other instrument of suitable mass resolution (>1,000) and sensitivity.

The MS measures the ion current (number of ions) for both versions of the monitor peptide (natural and labeled) as a function of time. The ion current may be integrated over time (ideally for as long as the monitor peptide appears in the mass spectrum) for each mass species, and the integrated amounts of natural and isotope-labeled forms are computed.

Computation of Abundance of Each Monitor Peptide in the Sample (Step h)

A ratio is computed between the amounts of the labeled and unlabeled (natural) monitor peptides. Since the amount of labeled peptide added is known, the amount of the natural monitor peptide derived from the sample digest can then be calculated by multiplying the known concentration of labeled monitor peptide by this measured ratio. By assuming that the amount of the monitor peptide in the digest is the same as (or closely related to) the amount of the parent protein from which it is derived, a measure of the protein amount in the sample can be obtained.

In order to detect and compensate for variation in the completeness of the sample digest process, a series of digest monitor peptides can be selected that indicate the progress of the digestion process. Digestion completeness can vary due to differences between sample digests in the ratio of proteolytic enzyme to plasma protein, to differences in time and temperature of digestion, to differences in the samples' endogenous protease inhibitor content, or to differences in the levels or activation of endogenous proteases. Specifically, one can carry out a time-course experiment in which a plasma sample is digested by trypsin (after reduction and alkylation of the plasma proteins), and the amounts of each of a series of peptides released can be measured as a function of time. Some peptides are released early in the course of the digest, probably because they are located at the surface of the target protein and because the cleavage sites at the peptides' ends are exposed to the protease, and reach their maximum final concentration in the digest early. Other peptides are release later during the course of the digestion, probably because they form part of the core of a target protein or because the cleavage sites defining the peptides' ends are not exposed at the surface of the intact target protein, and thus these peptides appear later during the course of digestion and reach their maximum final concentration later. It also occurs that some tryptic peptides are released from target proteins that are then further cleaved in solution, leading to an increase in a peptide's concentration in the digest followed by a decrease later as the peotide is further cleaved to other shorter peptides. By measuring the time vs concentration profiles of a series of specific peptides during such a time course, one can select digest monitor peptides that together give an accurate measure of the status of the plasma digestion process. The utility of a panel of such peptides is increased if they are products of one or a few proteins, so that abundance ratios between the peptides are reflective of the digest progress and not of the differences in concentration between the parent proteins. By measuring the selected digest monitor peptides in subsequent individual sample digests, one can compute where in the process of digestion each sample was arrested, effectively generating a standardized scale of digestion progress for the sample type involved. This information, in combination with knowledge of the time course for release of each monitor peptide to be used in sample analysis (relative to release of the digest monitor peptide in a reference digest), will allow corrections to be applied to monitor peptide abundances when specific samples are not digested to exactly the sample extent.

The specificity and sensitivity of the approach can be further enhanced by use of a multistage peptide capture methodology. In one embodiment of a multistage approach two different sequential capture steps can be used based on a first capture on an antibody raised to the N-terminal portion of the peptide and, after elution from this first antibody and neutralization, capture on a second antibody (A2) raised against the C-terminal portion of the peptide. Such N-term or C-term antibodies can be made because the immunogen typically used to make antipeptide antibodies consists of the peptide coupled to a large carrier protein (e.g., keyhole limpet hemocyanine or albumin) through a cysteine residue appended to the sequence of the desired monitor peptide (often spaced apart from the monitor peptide sequence by some spacer residues). If the cysteine is included at the N-terminus of the immunizing peptide, causing the N-term to be attached to the carrier surface, the C-terminus of the monitor peptide sequence will be exposed for recognition and antibody generation. Conversely, if cysteine is included at the C-terminus of the immunizing peptide, causing the C-term to be attached to the carrier surface, the N-terminus of the monitor peptide sequence will be exposed for recognition and antibody generation. Since antibodies often recognize a stretch of 3 to 6 amino acids, and since the monitor peptides are often 8 to 15 amino acids long, there is a high probability that the epitopes recognized by the N-term and C-term antibodies will be substantially different, thus offering separate but specific recognition of the monitor peptide. Any impurities (other peptides) that bind to the first (e.g., N-term) antibody through some similarity to the N-terminal portion of the monitor peptide sequence are very unlikely to bind also to the C-term antibody. Using two separate enrichment processes will in general give a purification equal to the product of the two separate enrichment steps: if the N-term antibody binds 1 part in $10^4$ of the digest peptides (as impurities, i.e., apart from the desired monitor peptide) and the C-term antibody also binds 1 part in $10^4$ of the digest peptides (as impurities, i.e., apart from the desired monitor peptide), then the sequential combination of these antibodies as two separate enrichment steps is likely to bind 1 part in $10^8$ of the non-monitor peptides. If both the N-term and C-term antibodies bind a high proportion of the monitor peptide (e.g., 90% at each step), then the final result of the two-stage capture would be 81% of the monitor peptide recovered, with only 0.000001% (1 part in $10^8$) of other peptides bound.

Other multistage enrichment processes can also be beneficial. A first antibody can be raised either against a surface peptide or else against the whole protein) can be used to capture the native protein from plasma after which the protein can be digested to peptides, and a monitor peptide captured by a second anti-peptide antibody.

Alternatively a sequential digestion approach can be used in combination with two anti-peptide antibodies. Here the plasma sample is digested with a first protease yielding a first version of a monitor peptide sequence that is bound by a first anti-peptide antibody. Following elution of this peptide, it is cleaved by a second protease, yielding two (or possibly more) new peptides, each of which has at least one new terminus (the prior C-term segment of the first monitor peptide has a new N-terminus, and the prior N-term segment has a new C-terminus). A second anti-peptide antibody is used to capture one of these newly exposed terminal sequences (a terminus that was not exposed prior to the second digestion step) for MS detection. One implementation of this approach would, as an example, involve selection of a monitor peptide sequence bounded by lysines and/or N- or C-termini, and within which there was one arginine residue. Using lys-C (which cleaves preferentially at lysine residues, but not arginine) as the first protease, a first anti-peptide antibody would be made to recognize the C-terminal lysine portion of the sequence (e.g., immunizing peptide linked to carrier via N-term cysteines). A second digestion, carried out with trypsin (which cleaves at both lysine and arginine) would cleave at the internal arginine in this peptide, creating two fragments, one of which has a new C-terminal sequence (ending in arginine) and which would be recognized by the second anti-peptide antibody. This approach actually makes use of three specificity steps (first antibody, second protease, second antibody) to further increase the overall specificity of the final detection process. In using a two-protease multistage system, the opportunity exists to capture and detect two (or more, if the second protease cuts more than once) "daughter" peptides separately as mutually confirmatory assays. Any combination of proteases with different specificities could be used.

A particularly interesting instance of the two-protease multistage system is one in which the action of the first protease occurs in vivo, generating a cleavage in a fraction of the native protein molecules in the sample. The action of such a protease could be an indication of a disease process or of a beneficial response to therapy, for example. One desired measurement would be the fraction of the molecules that were cleaved. This can be achieved by digesting the plasma sample with a protease (the in vitro protease) that does not cleave at the site of the in vivo protease, generating fragments of the native protein (peptides), one of which contains the in vivo cleavage site. An anti-peptide antibody directed to the N-terminus (or alternatively the C-terminus) of the monitor peptide can capture both the entire monitor peptide and the shorter version arising from in vivo cleavage. The ratio in abundance between the long and short forms of the monitor peptide (obtained preferably by quantitating each against an identical stable isotope labeled internal standard peptide) gives the ratio of the uncleaved to in vivo cleaved forms of the parent protein.

All of the multistage processes described above can make use of isotopically labeled peptides as internal standards, in the same way they are used for quantitation of peptides by the first single-analyte embodiment.

Automation of the Basic Implementation (2:)

Steps d, e, f and g of the basic implementation are preferably combined into an automated process, using a computer-controlled fluid handling system for steps d, e, and f, and a computer-controlled mass spectrometer for step g. In this approach the computerized fluid handling system carries out the reduction and alkylation of the sample, addition of trypsin, incubation, quenching of the trypsin activity, and addition of the labeled peptide standard(s).

In one version, the computerized fluid handling system then applies the prepared digest sample to an antibody (preferably on a solid support) specific for a monitor peptide, removes the digest, washes the antibody on its support, and finally elutes the captured peptides directly into the mass spectrometer for step g. The elution can be carried out in a very small volume (e.g., 10 ul) and thus the entire eluted sample can be instilled into the MS for maximum sensitivity. Alternatively step f can be carried out offline, generating a series of enriched peptide samples that can be introduced into a mass spectrometer later for measurement. This approach may be particularly appropriate when a MALDI MS is to be used for detection and quantitation of the peptides, since a MALDI target plate holding hundreds of samples can be prepared offline and introduced at a later time into the MS.

The entire process of steps a-h can be carried out as a unified analytical process for the quantitation of proteins in a sample.

Parallelized Embodiments for Multiple Analyte Measurement

In a first parallelized embodiment, multiple proteins can be measured using individual antibodies to select individual monitor peptides one at a time, in an apparatus that allows successive antibodies to be eluted at intervals into the MS (each monitored peptide is measured in succession as its antibody is put in position for elution). In this version, instead of a chromatography separation to separate a mixture containing a series of monitor peptides (in each case together with their added isotopically labeled versions), one uses a fluidic or mechanical means to place each antibody, on its solid support, into the elution path (typically a liquid stream of 10% acetic acid eluent directed into the MS). This version of the basic embodiment can be implemented using a multiplicity of small antibody columns arranged like the chambers of a revolver, as shown in FIGS. 1-7.

In this embodiment, two of the most time consuming and expensive processes are the preparation of the digested microsamples, and the preparation and use of the immobilized antibody surfaces that bind the peptides to be analyzed. Therefore one would like to prepare only one or a very few digests of a sample to be analyzed, and apply it to as many immuno-absorptive supports or surfaces as is efficient and necessary to measure the desired number of monitor peptides (target proteins). Since binding is diffusion related, an objective is to spread the peptide digest samples over a relatively large surface, and to both apply and remove it efficiently. Two limitations are evident at the outset. The first is the capacity and polyspecificity of the absorptive surface, and the second is the limitation of the mass spectrometer to simultaneously quantitate a large number of different analytes when increasing the number to be detected results in their greater dilution. Thus, if a maximally polyvalent absorptive surface is used, then its capacity for any one analyte is very small, and only a very small amount of each binding agent will be present. And as the number of analytes rises to a large number, the MS may not be able to resolve all the substances present. In the present embodiment incorporating automation, the objective is to arrange for digested samples to pass over a series of different immunoabsorptive supports, each containing one or a number of different specific antibodies, in a closed system in such a manner that all the supports are exposed to the samples, and are then washed free of excess sample. After this step, the discrete supports are separated, and each support eluted separately and efficiently into an electrospray MS system. The immunoabsorptive supports must be designed in such a manner that the attachment of antibodies to large sets of them (i.e., the critical step of their manufacture) may be done in parallel, and with a high degree of reproducibility.

In the initial design sixteen different immunoabsorptive supports comprising differing surfaces are used, and it is anticipated that a mixture of ten different antibodies will be attached to each, giving a total of 160 different proteins to be analyzed for in each assay set. Each antibody binding surface comprises the lumen of a hole in a plate (here a circular plate), and the lumen's surface area is increased by fluting. FIG. 1 illustrates the fluting of the antibody-containing holes or tubes to increase surface area.

Figure 2:
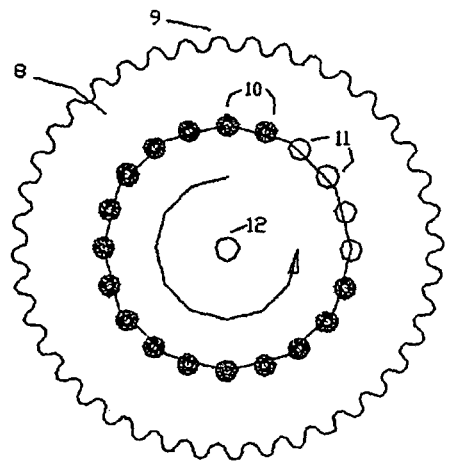
FIG. 2 shows the arrangement of binding surfaces in holes in disc 8 containing teeth 9 to allow its controlled rotation. Shown are sixteen antibody-containing holes 10, and four clear holes 11, aligned around axis 12.

FIG. 2 shows the arrangement of binding surfaces in holes in disk 8 containing teeth 9 to allow its controlled rotation. Shown are sixteen antibody-containing holes 10, and four clear holes 11, aligned around axis 12.

Figure 3:
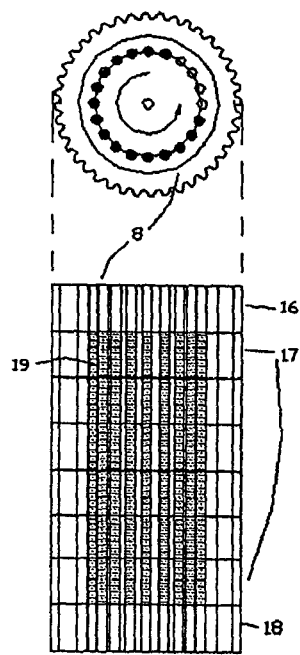
FIG. 3 shows how a set of discs 8 are aligned as stack 17 with clear aligned end caps 16 and 18. Bound antibodies are shown as 19.

FIG. 3 shows how a set of disks 8 are aligned as stack 17 with clear aligned end caps 16 and 18. Bound antibodies are shown as 19.

Figure 4:
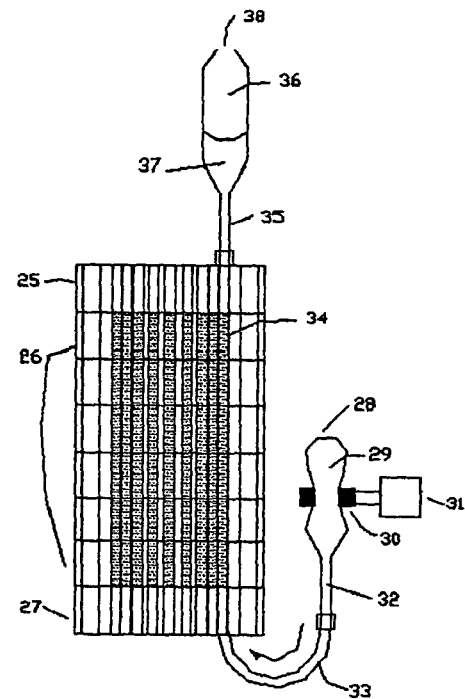
FIG. 4. An arrangement for aligning and loading the discs is shown in FIG. 4 where antibody solution 29 in bulb 28 is alternately squeezed and expanded by device 30 driven under computer control by 31 to push the liquid back and forth through tubes 32,33 and 34, and up through tube 35 into bulb 36. The solution pushed through 37 does not build up pressure in bulb 36 because of the presence of hole 38. Antibodies can thus be applied to a single hole of each of a series of disks, and process repeated to apply antibodies (typically of different specificities) to the other holes. The fluted lumen surfaces are chemically modified so as to bind the antibodies. Once the antibodies are applied the holes can be washed and the antibodies dried in place. The stack of disks is then disassembled to yield a series of identical antibody-loaded peptide capture disks.

An arrangement for aligning and loading disks is shown in FIG. 4 where antibody solution 29 in bulb 28 is alternately squeezed and expanded by device 30 driven under computer control by 31 to push the liquid back and forth through the tubes 32, 33 and 34, and up through tube 35 into bulb 36. The solution pushed through 37 does not build up pressure in bulb 36 because of the presence of hole 38. Antibodies can thus be applied to a single hole of each of a series of disks, and the process repeated to apply antibodies (typically of different specificities) to other holes. The fluted lumen surfaces are chemically modified so as to bind antibodies. Once the antibodies are applied the holes can be washed and the antibodies dried in place. The stack of disks is then disassembled to yield a series of identical antibody-loaded peptide capture disks.

In use, as shown in FIG. 5, disk 39 is held as 40 between clear disks 41 and 42, containing aligned holes. The arrangement keeps disks 41 and 42 stationary while disk 40 can be rotated by engagement of external means with teeth 9.

The operation of the system in one analytical cycle is shown in FIG. 6, where disk 63 with teeth 64 contains sixteen antibody-containing holes 65 and four clear holes 70-73. The antibody-containing holes are alternatively connected by slots in the upper and lower clear disks, with the lower slots indicated by dashed line 66 and the upper connections by non-dashed lines 67, making a continuous path connecting inlet 68, through all the antibody-containing holes 65 via the serpentine connections of over (67) and under (66) connecting slots, and exiting through 69. This allows a sample digest to be pumped back and forth through all the holes, then expelled, and the hole-set washed. These elements are shown in FIG. 6*b* as a circular cross-section through the disks. In next operation, the rotatable disk 63 is moved such that the antibody loaded tube 69 is aligned with tube 70 of plates 41 and 42, and a wash solution is run through. Indexing one step forward moves tube 69 to position 71 where an eluting solution, such as 10% acetic acid, is used to detach the bound peptides and transport them to a mass spectrometer, or intermediate capture point, such as reverse phase column. A next indexing brings tube 69 into register with position 72 where a buffer is run through to recycle the antibody and render it stable after exposure to the eluting solution. Each different antibody-containing tube (or hole) is thus indexed through the stations, resulting in a sequence of 16 successive elutions into the MS.

FIG. 7 indicates how the entire system is integrated, with the mass spectrometer 74 attached to disk analyzer 75, in turn fed samples by autosampler 76, all under control of computer 77.

The antibody-containing holes can be formed so as to carry antibodies (or other binding agents) on their inner surfaces (as shown) or they can be filled with a porous monolithic material to which the antibodies are bound, yielding a larger surface area and thus a higher local concentration of antibody molecules. Such monolithic supports can be formed by polymerization in situ, by sintering pre-made particles, by insertion of a preformed porous rod into each hole with a friction fit, or by other methods. In the case of antibodies bound to inner surfaces, these surfaces can be cylindrical (as in a normal tube) or they can be reticulated in various ways to increase inner surface area.

In clinical chemistry where a number of different analytical components such as the disks must be used, the most serious problem is that of being sure that the component in place is the correct one. Note that built into this system is an inherent capability for quality control and positive identification of binding sites. This is achieved as an automatic feature of the system because a mixture of standards is added to each peptide digest sample, only some of which bind to each antibody loaded binding surface. The analysis of the peptides eluted from each surface (hole) by the mass spectrometer therefore provides positive identification of the antibodies on that surface, and their operational condition. This aspect assures that the disk contains the correct antibody specificities. An added optional feature is the loading of the antibodies in each hole with their corresponding peptide during manufacture: in this case each hole in the disk could be eluted into the MS before any samples are loaded, and the antibody specificities confirmed by MS identification of these eluted peptides.

Alternatively the multiple-antibody-separate-elution approach can be implemented in other ways, for example employing electromagnetic means to move antibody-coated diamagnetic particles through the required positions (sample, wash, elution into MS). Arrays of immobilized anti-peptide antibodies, arranged on a flat surface so as to capture peptides from an overlying fluid volume; arranged on pins so as to capture peptides from a vessel into which they are dipped; or arranged in separate microvessels of a microfluidics device so as to be connectable into multiple fluid flowpaths can also be used. A multiplicity of mechanical and electromagnet solutions will be apparent to the problem of exposing multiple, separately immobilized antibodies to a sample, washing them and then eluting them individually by exposure to a stream of liquid that then moves into an MS.

Figure 8:
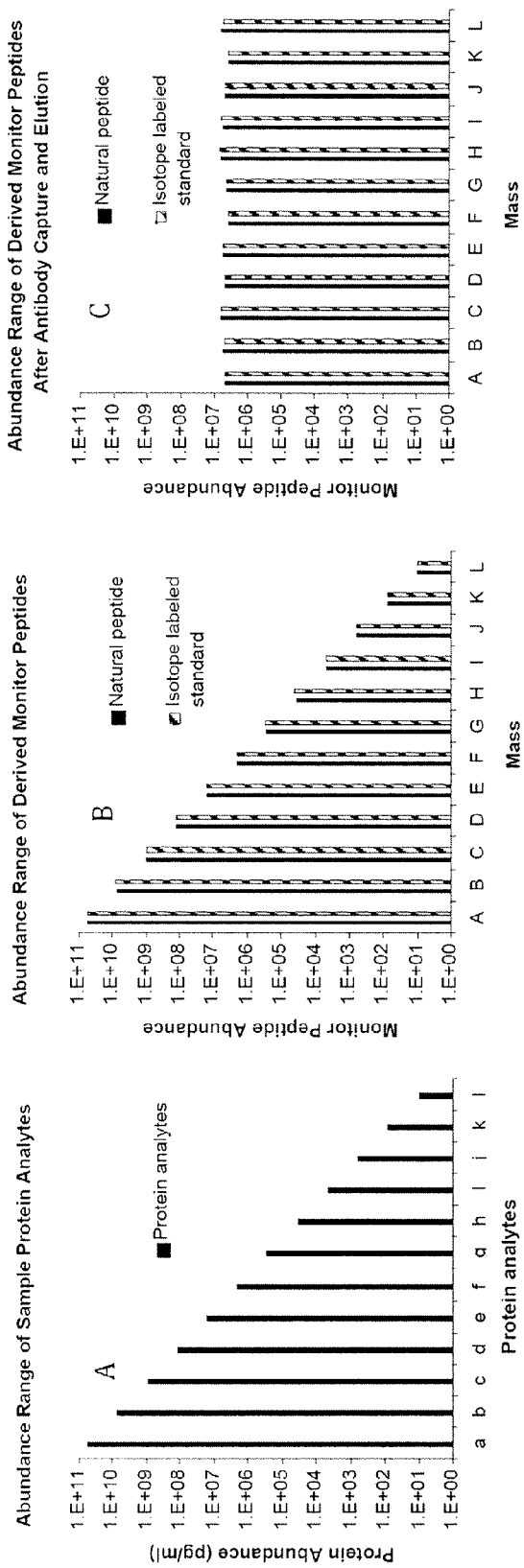
FIG. 8 illustrates the abundances of a series of peptide analytes having a wide range of concentrations in a sample digest (A), addition of internal standard peptides in concentrations similar to the expected analyte concentrations (B) and the equalization of these concentrations after capture and elution from antibody binding media.

In a second parallelized embodiment, the approach is applied to a series of monitor peptides (A-L) of different masses, for measurement of a series of proteins (a-l), at once (FIG. 8A). In this case a cocktail of labeled peptides in pre-determined amounts (based on expected relative abundances of the respective proteins in the sample) would be added to the sample digest (FIG. 8B: solid bars represent the natural peptide, and dashed bars represent the added stable isotope labeled monitor peptides). A series of capture antibodies would be used to capture just these monitor peptides (natural and labeled forms). These antibodies (on appropriate solid phase media) would preferably be combined in relative amounts so as to capture approximately equal amounts of each monitor peptide, irrespective of the amount of these peptides in the digest, thus resulting in an approximately equimolar mixture of monitor peptides upon elution into the MS (FIG. 8C). If the antibodies are of high affinity, then this objective can be achieved by preparing a column, or other affinity support on which approximately equal amounts of each antibody are fixed, and passing over this support enough sample digest so that all the antibodies can bind to saturation. If one or more of the antibodies has a lower affinity, then more of that antibody may be required in order to achieve approximately equal stoichiometry of captured and released peptides. Most of the mass of abundant monitor peptides will therefore not be bound (exceeding the amount of capture antibody on the support), but the low abundance peptides may only just saturate the respective capture antibody with none appearing in the flow-through (unbound) fraction. By rendering the monitor peptides more nearly equal in abundance (as compared to the very different abundances they might have in the sample digest), the dynamic range limitations of the LC and the MS cease to be major problems. This combination of monitor peptides can then be analyzed directly by introduction to the MS, provided that the masses of the monitor peptides (both natural and labeled forms) are different enough to allow the MS to resolve and quantitate all monitor peptides (in both forms) individually. Rendering a series of monitor peptides more nearly equimolar is a major advance in allowing multiplex (multianalyte) measurement by mass spectrometry.

Alternatively the combined monitor peptides could be subjected to LC/MS such that only one or a few monitor peptides were introduced into the MS at a time, and the MS could be pre-programmed to look for each monitor peptide in succession. Thus, in order to measure a series of monitor peptides (representing a series of protein analytes), all the corresponding isotopically labeled peptide standards are added to the digest (prepared as above by the computerized fluid handling system), and then the eluted peptides (now consisting of a series of monitor peptides with their corresponding labeled standards) are introduced into a chromatography column (such as a C18 reverse phase column, forming part of a chromatography system also under computer control) and eluted from this reverse phase column (typically over 5 to 30 minutes) by a gradient (typically of 0-70% acetonitrile in water with 0.05% trifluoroacetatic acid). The output (eluate of the column) is directed into the mass spectrometer, with the result that only one or a few of the monitor peptides appear at any one time, thus allowing the MS to measure each individually without the potential for interference of the other monitor peptides. An initial run is performed during which the elution time of each monitor peptide is determined by scanning the masses of all the eluted peptides. In subsequent runs, the LC/MS system can be programmed to look at the right elution time for peptides of the known masses of the labeled and unlabeled version of the monitor peptides, thereby allowing more measurement time to be directed to the desired monitor peptide measurements rather than scanning all peptide masses.

In this way the disclosed method using capture antibodies for enrichment can be parallelized to allow measurement of many proteins, and a series of proteins of very different relative abundances in the sample can be quantitated in a single MS or LC/MS operation. The equalization of the abundances ("stoichiometry flattening") of the monitor peptides is the key concept, and it overcome a key problem with MS quantitation, namely the limited dynamic range available with current systems.

Figure 9:
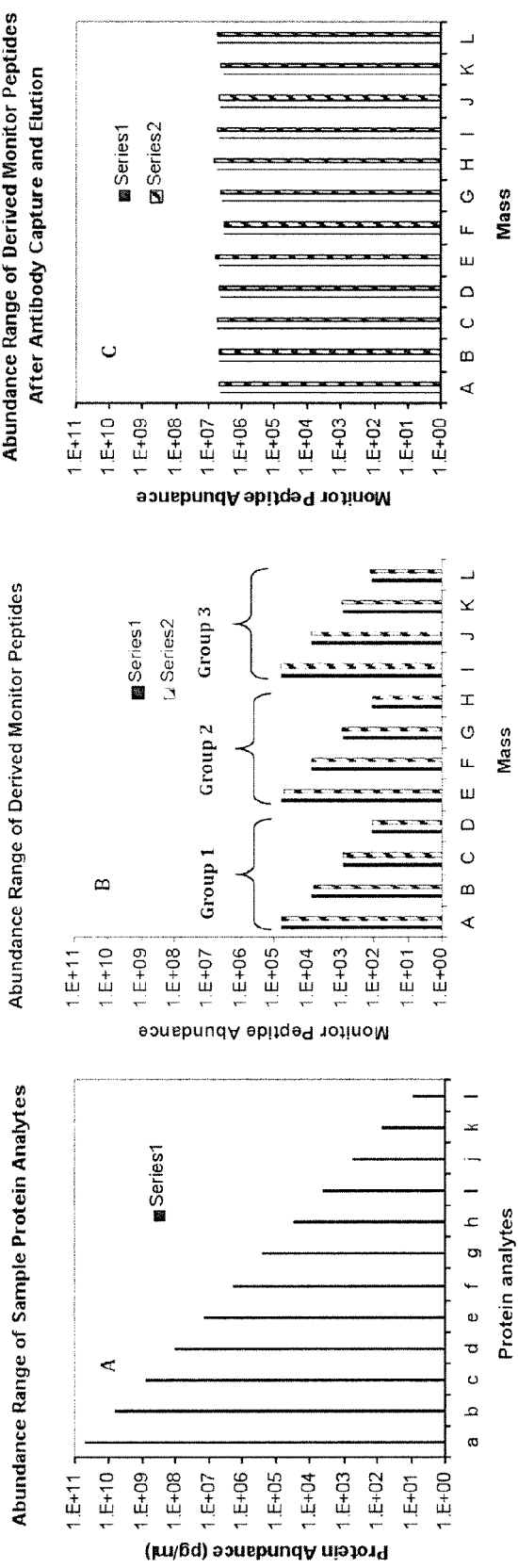
FIG. 9 illustrates how groups of peptide analytes occurring at similar concentrations can be treated together so as to economize on usage of internal standards.

In a third parallelized embodiment, a series of proteins are to be measured that have very different abundances in the sample, but we wish to economize on the use of labeled monitor peptides for the abundant proteins (FIG. 9). For example, serum albumin, complement C2 and thyroglobulin differ in abundance in human serum by steps of approximately 1,000-fold (relatively $10^6:10^3:1$ in concentration). If a sample of plasma is digested to peptides with an enzyme such as trypsin, then the monitor peptides derived from these three proteins will also differ in abundance by the same factors (assuming complete digestion). Now the basis of the quantitative method proposed is to 1) choose at least one peptide of suitable chemical properties to represent each protein to be measured (the monitor peptide); 2) add an isotopically labeled version of each monitor peptide at a concentration similar to that of the natural (sample-derived) peptide, thereby providing an internal quantitative standard distinguishable by mass in a mass spectrometer but otherwise chemically the same as the natural peptide; 3) enrich each monitor peptide (natural plus isotope labeled standard) by capture on a specific anti-peptide antibody and elution after washing; and 4) analyze the enriched monitor peptides in a mass spectrometer to determine the ratio of natural versus isotope labeled peptide detected. This ratio gives the quantity of the original analyte protein in relation to the amount of added isotope labeled standard.

In this embodiment, it is noted that since it is optimal to add the labeled peptide standards (dashed bars, Series 2 in FIG. 9) at a concentration similar to that of the equivalent natural peptide (solid bars, Series 1 in FIG. 9); i.e., that the internal standard be present at a similar concentration to the monitor peptide to be quantitated, then the albumin monitor peptide must be added at 1,000 times the amount of the C2 monitor peptide and 1,000,000 times the amount of the thyroglobulin monitor peptide (since these three proteins are typically present at these relative concentrations). Clearly the albumin monitor peptide, at 1,000,000-fold higher concentration, is over-abundant when the thyroglobulin peptide can be detected, and adding 1,000,000 times the amount required for the thyroglobulin monitor peptide is wasteful of the labeled albumin monitor peptide (which will typically be made by synthesis). Hence in this embodiment (FIG. 9C), three sub-samples of the plasma peptide digest are prepared: one undiluted (to which is add the required amount of the thyroglobulin labeled monitor peptide, and those of other proteins in Group 3 abundance class: FIG. 9), a second diluted about 1,000 fold (Group 2, to which we add about the same amount of the labeled complement C2 monitor peptide), and a third diluted about 1,000,000 fold (Group 1, to which is add the albumin monitor peptide). Thus diluted samples are created within which to detect groups of higher, middle and low abundance proteins, thereby requiring less of the corresponding labeled monitor peptides. After capture by the antibodies and elution, the peptides are recovered at nearly the same relative abundance (FIG. 9C).

In practice the number of groups (dilutions) will depend on the degree to which labeled peptides need to be conserved, and may be greater than three. In the preferred embodiment this principle is implemented by grouping the monitor peptides for various abundance classes of proteins in the sample, into 5 abundance classes, each of which covers only a 100-fold range of protein abundance (and which together span 10,000,000,000 fold in abundance). The labeled monitor peptides for each protein in a class are combined into a cocktail whose members are within 100 fold of one another (relative abundances set according to the expected relative abundances of the proteins in the sample). An undiluted aliquot and 4 dilutions of the sample peptide digest (each of 100-fold relative to the last) are prepared, and the 5 labeled monitor peptide cocktails are added to the respective dilutions prior to the enrichment and analysis steps (4 and 5 above). The method thus requires much less monitor peptide for high abundance proteins at the cost of running 5 analyses instead of one. For reasons set out below, this is compatible with other factors to be optimized, and that limit the number of peptides to be analyzed in one step anyway.

The major element of this embodiment is that peptides are grouped into classes according to the expected abundance of the respective target protein in the sample. The required abundance information is obtained from exploratory studies using the disclosed invention (scanning a series of such dilutions to see in which class a given monitor peptide can be detected) or from other quantitative measurements including published data. The necessary data is organized in a database and used with other criteria for the selection of optimal monitor peptide sets, making use of the ability of the database system to filter, rank and sort thousands to millions of candidate in silico peptides by complex criteria.

Figure 10:
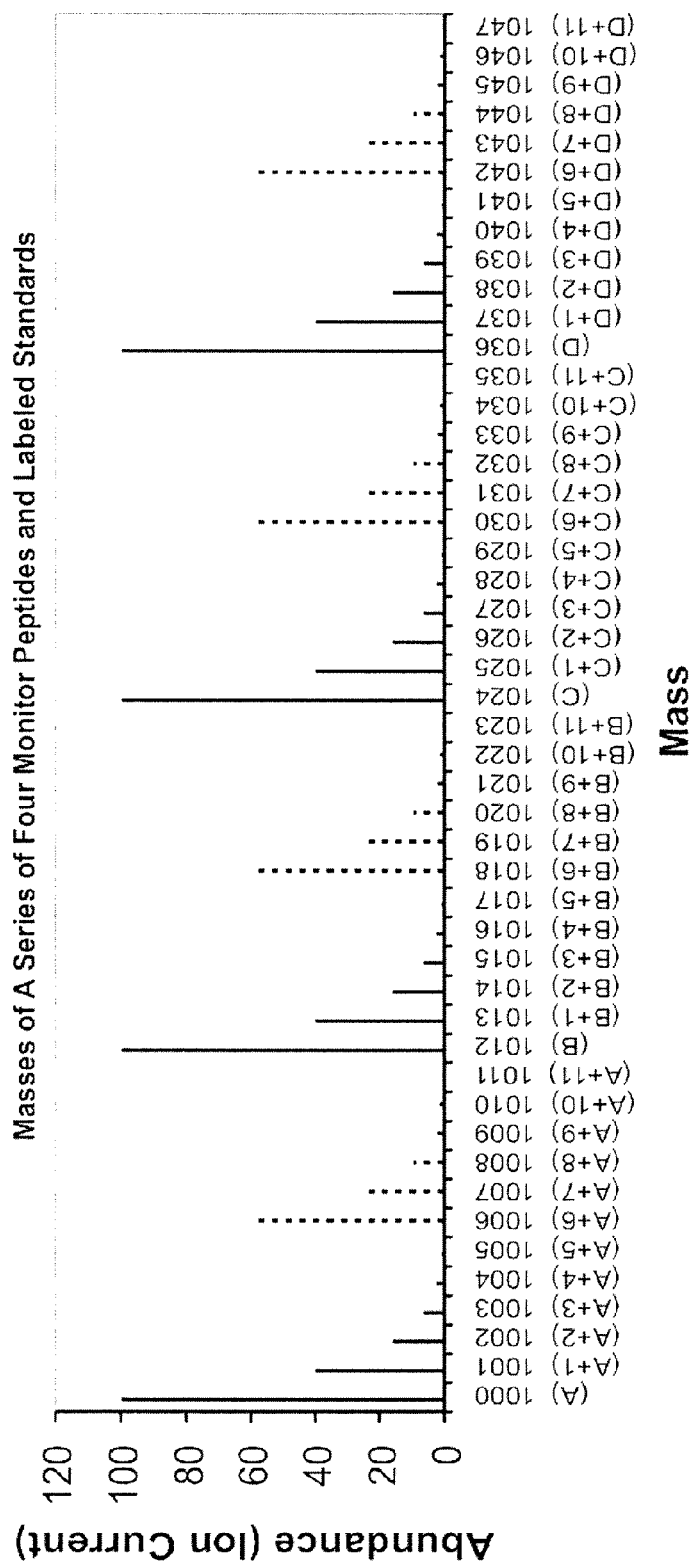
FIG. 10 shows how sets of monitor peptides (natural peptides a solid pars, labeled standards as hatched) can be selected from groupings that do not overlap in mass, and hence can be separately quantitated.

In a fourth parallelized embodiment (FIG. 10), the monitor peptides are grouped into classes based on peptide mass, in such a way that the peptides in a class do not overlap. An example of such a class criterion is as follows: assume the peptide selected as monitor peptide for protein a has mass A (in atomic mass units (amu) or daltons) and is for the sake of this example singly charged (i.e. is detected at an M/Z value of A), and that the corresponding isotopically labeled monitor peptide A has a mass of A+6, and that it can be assumed both peptides have a series of mass analogs in their spectra extending 5 mass units up from the parent masses (due to the well known incorporation of natural frequencies of various stable isotopes). The peptide peaks for these peptides will thus extend over the range {A, A+1, A+2, A+3, A+4, A+5} for the natural peptide (solid bars in FIG. 10) and {A+6, A+7, A+8, A+9, A+10, A+11} for the stable isotope standard (dashed b 10), or in other words over a range of A to A+11 amu. Assume then that one selects a monitor peptide B from another protein b that has a mass of A+12: none of the mass variant peaks of this peptide B will overlap peaks of the mass variants of the peptide A. Similarly one selects a series of monitor peptides ideally spaced at least 12 amu apart. Thus a series of 50 peptides could be placed in the mass range 1,000 to 1,600. In practice the peptides available for selection will not be ideally arranged and thus it is likely that no more than 10 might be combined to span the ideal measurement range without overlap. Thus these 10 proteins could be quantitated at once by the MS, and this class is a panel of simultaneously measurable proteins. Since the panel of peptides would be introduced into the MS at once, an MS that can efficiently scan the required range of masses at high duty cycle is desired. In the detection scheme disclosed, these 10 monitor peptides would be added to the natural sample peptide digest, and the corresponding 10 antibodies would be used together to enrich these 10 peptides for analysis.

The key element of this embodiment is the selection of mutually compatible sets of monitor peptides based on non-overlapping masses.

In a fifth parallelized embodiment, the third and fourth above are combined. Here we select classes of monitor peptides that satisfy both 1) similarity in parent protein abundance class in the sample, and 2) non-overlapping masses. These criteria may be applied in combination with the other criteria disclosed in the basic single-analyte embodiment (hydrophilicity, appropriate size, lack of certain amino acids, etc). The classes so developed are optimized for use in the disclosed measurement method. They maximize the number of proteins that can quantitated in one MS run and minimize the consumption of the typically expensive stable isotope labeled monitor peptides. The strategies for allowing multiple monitor peptides to be detected at once can be combined with the automation methods to allow large numbers of analytes to be routinely measured.

Other Embodiments

A series of additional embodiments make use of anti-peptide antibodies in alternative methods.

Another embodiment makes use of experimentally observed partial peptide sequence data obtained as "de novo" sequence by MS/MS techniques for monitor peptide design, instead of sequence derived from an existing database.

Figure 11:
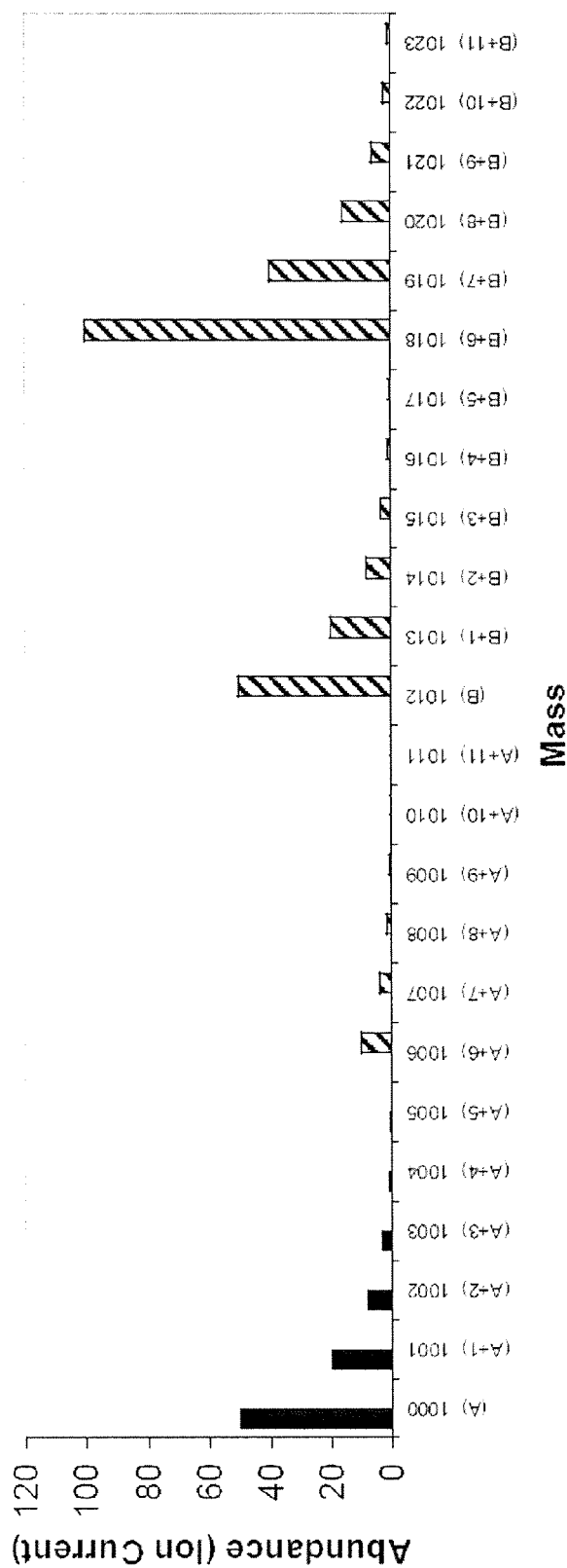
FIG. 11 illustrates the use of multiple internal standard peptides of different masses at different concentrations to provide a working curve for quantitation of a sample peptide analyte.

Another embodiment (FIG. 11) uses multiple isotopically labeled peptides for a given monitor peptide analyte, added at a series of levels to create a standard curve. In this embodiment, two or more versions of each monitor peptide are synthesized having different isotopic masses. If the peptide sequence contained 3 histidines for example, one version of the peptide (IV1) might contain a single isotope-labeled HIS residue (6× carbon-13; net 6 dalton heaver than natural), while a second version (IV2) contained two, and a third version (IV3) contained all three histidines as heavy isotope versions. The three modified peptides would thus be 6, 12 and 18 daltons heavier than the natural version. One could then add to the sample an amount of IV1 equal to ⅕ the expected amount of the natural version, an amount of IV2 equal to the expected natural level, and an amount of IV3 equal to 2 times the natural level. The MS spectrum of the monitor peptide would thus display four separately resolved versions, with the three isotopically labeled versions providing an internal standard curve covering a 10-fold range around the expected value. In this way the monitor peptide could be measured against an internal standard curve in every sample. Obviously any combination of labeled amino acids and appropriate isotope labels could be combined to design labeled monitor peptides that differ from the natural peptide and one another by any of a range of mass increments.

Another embodiment makes use of specific properties engineered into the monitor peptides specifically designed to facilitate labeling with oxygen-18. In this case (assuming that trypsin is used as the fragmenting enzyme) an extended version of the monitor peptide could be synthesized without isotopically labeled amino acids, but in which the added c-term residues begin with a Lys or Arg residue (e.g., nterm-MONITOR-lys-gly-ser-gly-cys-cterm as in the first preferred embodiment). By cleaving this peptide with trypsin in the presence of oxygen-18 water, two atoms of oxygen-18 (4 daltons heavier than natural) would be introduced into the final monitor peptide. The advantage of this approach is that only a single version of the monitor peptide would need to be made: the same extended version could be used for immunization, for affinity purification of the antibody, and as the MS internal standard (after cleavage and oxygen-18 introduction), thereby potentially reducing cost. Other similar constructs can be constructed appropriate for cleavage by other enzymes if their mechanisms of cleavage are amenable to the introduction of isotope labels.

Another embodiment makes use of isotopically-labeled monitor peptides prepared by labeling natural peptides (derived from digestion of a reference sample) instead of chemical synthesis (as described in the first preferred embodiment). In this approach, a reference sample of the type to be analyzed subsequently is digested with the same enzyme or reagent as will be used on subsequent samples (e.g., trypsin) to yield peptides. These peptides are then reacted with a chemical derivatizing agent containing an isotopic label. For example, the peptides may be reacted with deuterated iodoacetamide, thereby introducing a label on all cysteines-containing peptides. Alternatively the sample proteins could be reduced and alkylated with deuterated iodoacetamide prior to cleavage by trypsin. Samples to be analyzed would be reduced and alkylated with unlabeled iodoacetamide, so that the sample and labeled monitor peptides would be chemically the same. The labeled monitor peptide mixture (essentially the labeled digest of the reference sample) would be added to the digest from a test sample, typically in equal proportions, and the resulting mixture subjected to antibody enrichment of the selected monitor peptides. In this case the monitor peptides would be selected from among the cysteine containing peptides of the target protein. The resulting MS readout would reveal the ratio in abundance for the monitor peptide (and hence target protein) between the reference sample and the test sample. Since in this embodiment the label is introduced through a chemical modification of the monitor peptide, the enrichment antibody is preferably raised by immunization with a similarly modified peptide: the peptide immunogen would be a cysteines-containing peptide in which the cys was alkylated with iodoacetamide. Other chemical means can be used to introduce other labels on various amino acids, or into the n-terminal or c-terminal groups specifically. In each case, the same modification would be made to the test sample peptides (either before or after digestion, as appropriate, but without the isotope label) and the antibody would be created against the appropriately modified synthetic peptide.

Alternatively a phage-display or other in vitro technique can be used to select antibodies against the monitor peptide.

A further embodiment makes use of monoclonal antibodies, phage display antibodies (single chain or Fab), single domain antibodies, affibodies, or other chemically uniform proteins as peptide binding reagents.

In a further alternative, the immunizing peptides are prepared from a digest of the parent protein, rather than by chemical synthesis.

In a further alternative, the immunizing peptides are synthesized as fusion proteins in an expression system (such as E. coli, baculovirus, yeast) or an in vitro translation system (such as rabbit reticulocyte, wheat germ or E. coli lysate), rather than by chemical synthesis. The desired peptides can be produced in multiple copies in the fusion protein if desired, can be isolated through an incorporated affinity tag (e.g., the FLAG peptide, or a polyhistidine tag), and can be subsequently cleaved from the fusion protein (e.g., via trypsin) and purified by liquid chromatography or other methods. The isotopically labeled monitor peptides can be made by similar means through the incorporation of labeled aminoacids into the synthesis system.

In a further alternative, the enriched monitor peptide (natural plus isotope labeled) is applied to a target for MS analysis in a MALDI mass spectrometer.

A further embodiment makes use of fluorescence detection instead of MS detection, and uses covalent fluorescent labels (e.g., cysteines-reactive Cy3 and Cy5 dye labels) to label the sample peptides and the added monitor peptides. In this case, the antipeptide antibodies are created against dye-conjugated antigens and selected in such a way that they bind the two forms (e.g., Cy3 and Cy5) relatively equally. The final fluorescence ratio detection can be carried out directly upon elution of the peptides from the antibody (if the antibody is specific enough to reject all other peptides), or following another separation step (e.g., reverse phase LC or capillary electrophoresis) in which the Cy3 and Cy5 peptides behave, if not identically, at least in a reproducible and decipherable way (so that the dilution positions of the two version of the monitor peptide can be confidently predicted for measurement).

A further embodiment makes use of fluorescence detection in which a synthetic monitor peptide standard is labeled with the label (e.g., Cy5) and the sample digest remains unlabeled. In this embodiment the sample-derived monitor peptide competes with the fluorescently labeled standard peptide for binding to the corresponding anti-peptide antibody. The concentration of the sample-derived peptide can thus be inferred, using a standard working curve, from the amount of labeled standard peptide bound to and subsequently eluted from the antibody. At high sample concentrations of parent protein (high concentrations of monitor peptide in the digest) less labeled standard peptide will be bound, and vice versa. The fluorescently labeled standard peptides can then be separated and detected very sensitively using capillary electrophoresis, and particularly the multichannel devices developed for DNA sequencing (e.g., ABI 3700, Amersham MegaBACE).

Example

A database of 289 proteins detected in human plasma by various means was constructed by combining information from textbooks, catalogs of diagnostic assays, and a search of the scientific literature. Amino acid sequences for these proteins were downloaded and stored in a Microsoft Access database as text fields. Each protein sequence was processed in an Excel spreadsheet by a macro procedure that created a list of tryptic peptide fragments. A series of parameters was computed for each peptide sequence, including length, mass, expected net charge at neutral pH, total charged groups, Hopp Woods hydrophilicity (HWH) and normalized HWH (HWH/number of amino acids), and the numbers of Cys, Trp, Pro and Met residues. A first selection of usable peptides was made based on the following requirements evaluated by an Excel macro: length>7 and <14 residues, no Cys, Met or Trp residues, normalized HWH>−0.5 and <0.5, and mass>800. The results (peptide sequences, and computed parameters) were stored in the database. A total of 10,204 peptides were thus derived, of which 751 met the initial requirements.

For a proof of concept test, one monitor peptide was selected for each of four protein analytes: TNF, IL-6, hemopexin and alpha-1-antichymotrypsin. Where multiple peptides from a protein met the initial requirements, preference was given to peptides that contained a proline (as this is expected to increase immunogenicity). Synthetic peptides were generated for each sequence with a four residue extension (GSGC or CGSG) to allow coupling to keyhole limpet hemocyanine (KLH) carrier via a terminal Cys residue. In the case of the TNF alpha peptide, two versions of the monitor peptide were synthesized: one with an N-term extension and the other with a C-term extension (all other peptides carried a C-terminal extension). The peptide sequences (extensions underlined) were:

| | |
|---|---|
| IL-6 | residues 83-94 with C terminal extension GSGC |
| Hemopexin | residues 92-102 with C terminal extension GSGC |
| Alpha-1-Antichymo | residues 307-314 with C terminal extension GSGC |
| TNF-a C-term | residues 66-78 with C terminal extension GSGC |

Each peptide was coupled to an albumin carrier and injected into two rabbits according to a short immunization schedule. Antibody production is monitored via an ELISA assay using peptide immobilized on microwell plates. For each peptide, polyclonal antibody from the better of the two rabbit antisera (based on higher ELISA signal indicating more or higher affinity antibody) was immunoaffinity purified on a column of properly oriented peptide immobilized on thiol containing Sepharose.

Immunopurified antibodies were immobilized in an oriented manner on POROS protein G resin (Applied Biosystems). Once the antibody associated by specific interaction of protein A with the Fc portion of the antibody molecules, covalent crosslinking was achieved by exposure to dimethylpimerimidate (DMP) according to the manufacturer's instructions. The anti-peptide antibody POROS (APA-POROS) support was washed and stored at 4 C.

Capillary microcolumns (1 cm×100 microns) containing the supports are packed in pre-made frit-fitted capillaries (New Objectives) using a bomb pressurized with 1000 psig He. Supports carrying rabbit polyclonal AB to the first four peptides tested above were individually exposed to a mixture of the four respective labeled monitor peptides. The supports were washed and the bound peptides eluted using 10 microliters of 10% acetic acid to a capillary C18 referce phase column and thereafter eluted ionto the ESI source of a Qtrap (applied Biosystems) MS system by a 0% to 70% ACN gradient in 0.05 formic acid. On average, the antibody supports showed a 100-fold enrichment of the 'correct' monitor peptide.

What I claim is:

1. A method of quantifying an amount of at least a first monitor peptide and a second monitor peptide in a biological sample, comprising:
   contacting the sample with
   (i) a first anti-peptide antibody specific for said first peptide and;
   (ii) a known quantity of a labeled version of said first peptide;
   contacting the sample with
   (i) a second antipeptide antibody specific for said second peptide, wherein said second antibody is different from said first antibody and;
   (ii) a known quantity of a labeled version of said second peptide, separating peptides bound by said first and said second antibodies from unbound peptides;
   eluting said peptides bound by said first and said second antibodies from said antibodies;
   measuring the amount of said first peptide eluted from said first antibody using a mass spectrometer;
   measuring the amount of said labeled version of said first peptide eluted from said first antibody using a mass spectrometer;
   calculating the amount of the first peptide in the biological sample;

measuring the amount of said second peptide eluted from said second antibody using a mass spectrometer;

measuring the amount of the labeled version of the second peptide eluted from said second antibody using a mass spectrometer; and calculating the amount of the second peptide in the biological sample, wherein said biological sample is a proteolytic digest of a bodily fluid sample.

2. The method of claim 1, wherein at least one of said first and said second antibodies is a monoclonal antibody.

3. The method of claim 1, wherein at least one of said first and said second antibodies is a polyclonal antibody.

4. The method of claim 1, wherein said first and said second antibodies are both polyclonal antibodies.

5. The method of claim 1, wherein said first and said second antibodies are both monoclonal antibodies.

6. The method of claim 1, wherein the labeled version of the first peptide includes at least one site at which a stable isotope is substituted for the corresponding predominant natural isotope in more than 98% of peptide molecules.

7. The method of claim 1, further comprising: attaching the first antibody to a support.

8. The method of claim 1, further comprising: attaching the first antibody to a packed column.

9. The method of claim 1, further comprising: attaching the first antibody to a monolithic porous support.

10. The method of claim 1, further comprising: attaching the first antibody to a mesh.

11. The method of claim 1, further comprising: attaching the first antibody to magnetic beads.

12. The method of claim 1, wherein the first peptide and the second peptide are selected from among the set of peptides produced by digestion of the target protein to provide high signal to noise in the mass spectrometer.

13. The method of claim 1, further comprising:
preparing the labeled version of the monitor peptide.

14. The method of claim 13, wherein the labeled version of the monitor peptide includes a stable isotope.

15. The method of claim 1, wherein said first anti-peptide antibody is created using said first peptide or a nonmaterially modified version of the first monitor peptide.

16. The method of claim 1, further comprising: creating the first antibody using the first peptide or a non-materially modified version of the first peptide.

17. The method of claim 1, wherein the said bound peptides are subjected to a chromatography step after elution from said antibodies and before introduction into said mass spectrometer.

18. The method of claim 1 wherein said first and second peptides are proteolytically cleaved from first and second sample proteins, respectively, and wherein the amounts of said first and second proteins in said body fluid sample are calculated from the amounts of said first and said second peptides in the sample.

19. The method of claim 1, wherein said flit monitor peptide is a peptide fragment of TNF or IL-6.

20. A method for quantifying the amount of a peptide in a biological sample, comprising: contacting the sample with (i) an anti-peptide antibody specific for said peptide; (ii) a known quantity of a labeled version of the peptide, separating peptides bound by said antibody from unbound peptides eluting said peptide bound by said antibody from said antibody; measuring the amount of the peptide eluted from said antibody using a mass spectrometer: and calculating the amount of the peptide in the biological sample; wherein said biological sample is a proteolytic digest of a bodily fluid.

21. The method of claim 20, further comprising: preparing the labeled version of the peptide.

22. The method of claim 20, wherein the labeled version of the peptide includes at least one site at which a stable isotope is substituted for the predominant natural isotope in more than 98% of peptide molecules.

23. The method of claim 20, further comprising: creating the anti-peptide antibody using the peptide or a non-materially modified version of the peptide.

24. The method of claim 20, wherein said bound peptides are subjected to a chromatography step after elution from said antibody and before introduction into said mass spectrometer.

25. The method of claim 20, wherein the anti-peptide antibody is a polyclonal antibody.

26. The method of claim 20, wherein the anti-peptide antibody is a monoclonal antibody.

27. The method of claim 20 wherein said first and second peptides are proteolytically cleaved from first and second sample proteins, respectively, and wherein the amounts of said first and second proteins in said body fluid sample are calculated from the mounts of said first and said second peptides in the sample.

28. The method of claim 20, wherein the polyclonal antibody is created using the monitor peptide or a non-materially modified version of the monitor peptide.

* * * * *